US012678433B2

(12) United States Patent
Zhong et al.

(10) Patent No.: US 12,678,433 B2
(45) Date of Patent: Jul. 14, 2026

(54) COMPOUNDS FOR TREATMENT OF HEMOLYSIS-AND INFLAMMASOME-ASSOCIATED DISEASES

(71) Applicant: New York Blood Center, Inc., New York, NY (US)

(72) Inventors: Hui Zhong, New York, NY (US); Karina Yazdanbakhsh, New York, NY (US)

(73) Assignee: New York Blood Center, Inc., Rye, NY (US)

( * ) Notice: Subject to any disclaimer, the term of this patent is extended or adjusted under 35 U.S.C. 154(b) by 445 days.

(21) Appl. No.: 18/248,644

(22) PCT Filed: Oct. 13, 2021

(86) PCT No.: PCT/US2021/054827
§ 371 (c)(1),
(2) Date: Apr. 11, 2023

(87) PCT Pub. No.: WO2022/081742
PCT Pub. Date: Apr. 21, 2022

(65) Prior Publication Data
US 2023/0372330 A1 Nov. 23, 2023

Related U.S. Application Data

(60) Provisional application No. 63/160,351, filed on Mar. 12, 2021, provisional application No. 63/091,140, filed on Oct. 13, 2020.

(51) Int. Cl.
| | |
|---|---|
| *A61K 31/49* | (2006.01) |
| *A61K 31/555* | (2006.01) |
| *A61P 7/06* | (2006.01) |

(52) U.S. Cl.
CPC ............ *A61K 31/49* (2013.01); *A61K 31/555* (2013.01); *A61P 7/06* (2018.01)

(58) Field of Classification Search
CPC .. A61K 31/49; A61K 31/555; A61K 2300/00; A61K 31/357; A61K 31/4706; A61P 7/06; A61P 33/06; A61P 35/00; C07D 453/04; C07D 487/22
See application file for complete search history.

(56) References Cited

U.S. PATENT DOCUMENTS

| | | | | |
|---|---|---|---|---|
| 5,919,755 A | * | 7/1999 | Kangasaho | A61K 31/40 514/185 |
| 2002/0042043 A1 | | 4/2002 | Stassinopoulos | |
| 2009/0081231 A1 | | 3/2009 | Chevrier et al. | |
| 2012/0245136 A1 | | 9/2012 | Hadida-Ruah et al. | |
| 2017/0319517 A1 | * | 11/2017 | Bean | A61P 17/04 |
| 2020/0023011 A1 | * | 1/2020 | Feng | A61P 17/02 |

FOREIGN PATENT DOCUMENTS

| | | | | |
|---|---|---|---|---|
| CN | 111297861 A | 6/2020 | | |
| WO | WO-2018144845 A1 | * | 8/2018 | .......... C07K 14/795 |
| WO | WO 2020/219867 A1 | 10/2020 | | |

OTHER PUBLICATIONS

Yao, Signal Transduct Target Ther. Jan. 5, 2024;9(1). (Year: 2024).*
Cleveland Clinic (https://my.clevelandclinic.org/health/diseases/21624-autoimmune-diseases, 2024) (Year: 2024).*
MedicalNews Today, https://www.medicalnewstoday.com/ articles/metabolic-disorders, 2025 (Year: 2025).*
Whittemore, 2016, https://www.oregon.gov/oha/PH/HEALTHYPEOPLEFAMILIES/WIC/Documents/lawn/presentation-2016-05-metabolic.pdf (Year: 2016).*
Cleveland Clinic, 2025, https://my. clevelandclinic.org/health/drugs/19682-hemin-injection (Year: 2025).*
Greenwood, Journal of Antimicrobial Chemotherapy (1992, 30, 417-42) (Year: 1992).*
Adamson, Chem. Soc. Rev., 2021, 50, 3647-55 (Year: 2021).*
Kaushar, Int J of Immunopathology & Pharmacology, 35, 1-12, 2021 (Year: 2021).*
Johnson et al., (British J. of Cancer 2001, p. 1424-1431) (Year: 2001).*
Gura et al. (Science 1997, Nov 7, 278) (Year: 1997).*
Neidle, Stephen, ed., Cancer Drug Design and Discovery:(Elsevier/Academic Press, 2008) (Year: 2008).*
Cecil Textbook of Medicine, 20th Edition, vol. 1, 1996 (Year: 1996).*
Bensinger et al. (Arch Intern Med, 1974;133;(4):624-631). (Year: 1974).*
Adragna (J Membrane Biol, 142, 195-207, 1994) (Year: 1994).*
Yazdanbakhsh et al. (Blood, Jul. 19, 2012, vol. 120, 3). (Year: 2012).*
Guo et al., "Inflammasomes: mechanism of action, role in disease, and therapeutics," Nature medicine, Jul. 2015, 21(7):677-87.
International Preliminary Report on Patentability in International Appln. No. PCT/US2021/054827, mailed on Apr. 27, 2023, 9 pages.
International Search Report and Written Opinion in International Appln. No. PCT/US2021/054827, mailed on Jan. 19, 2022, 13 pages.
Mangan et al., "Targeting the NLRP3 inflammasome in inflammatory diseases," Nat Rev Drug Discov, Aug. 2018, 17(8):588-606.
Olupot-Olupot et al., "Hydroxyurea treatment is associated with lower malaria incidence in children with sickle cell anemia in sub-Saharan Africa," Blood, Mar. 23, 2023, 141(12):1402-10.

(Continued)

*Primary Examiner* — Umamaheswari Ramachandran
(74) *Attorney, Agent, or Firm* — Fish & Richardson P.C.

(57) ABSTRACT

Disclosed herein are methods of treating a complication of a hemolysis and/or an inflammasome activation-associated disease comprising administering to a patient in need thereof quinine, or a derivative or salt thereof, or the combination of quinine and hemin. Also disclosed is a method of reducing alloimmunization in chronically transfused subjects, comprising administering to a patient in need thereof a therapeutically effective dose of quinine.

15 Claims, 43 Drawing Sheets

(56) References Cited

OTHER PUBLICATIONS

Watanabe-Matsui et al., "Heme regulates B-cell differentiation, antibody class switch, and heme oxygenase-1 expression in B cells as a ligand of Bach2," Blood, The Journal of the American Society of Hematology, May 19, 2011, 117(20):5438-48.

* cited by examiner

FIG. 5

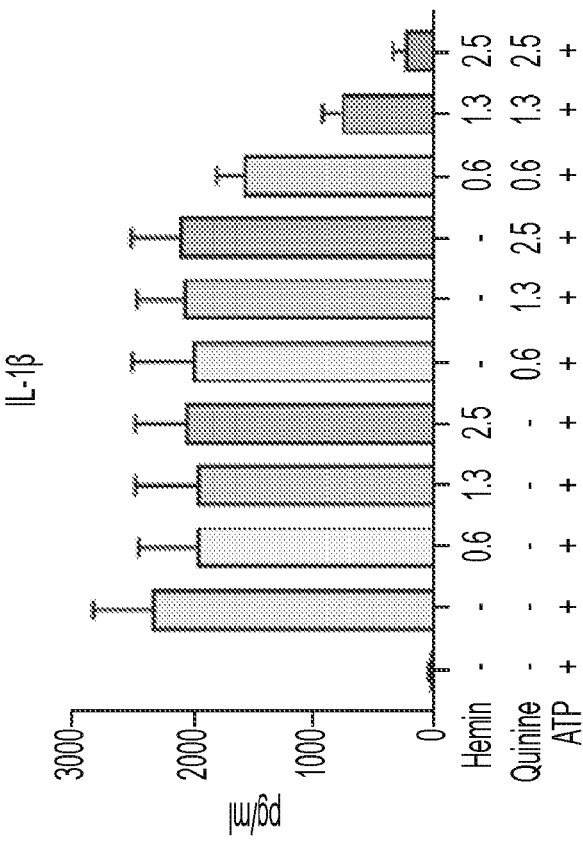
FIG. 13B
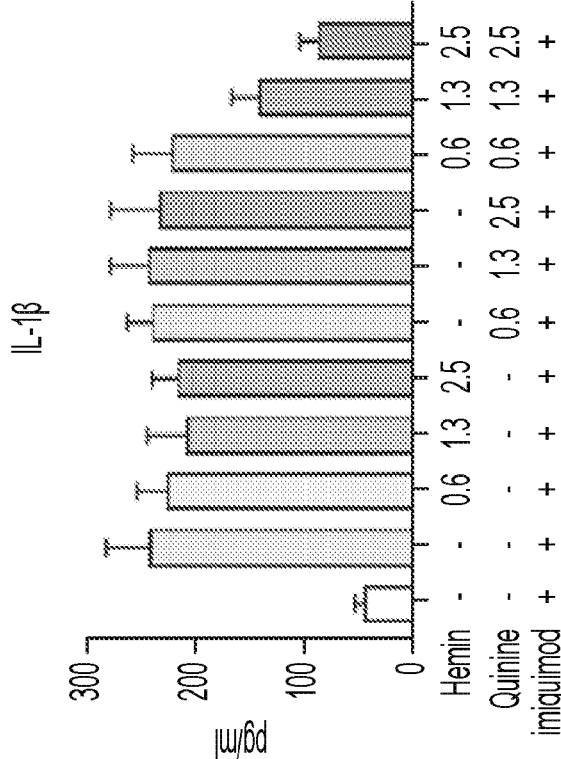

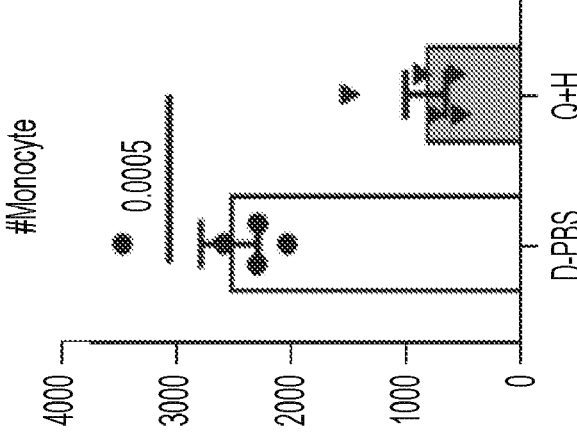
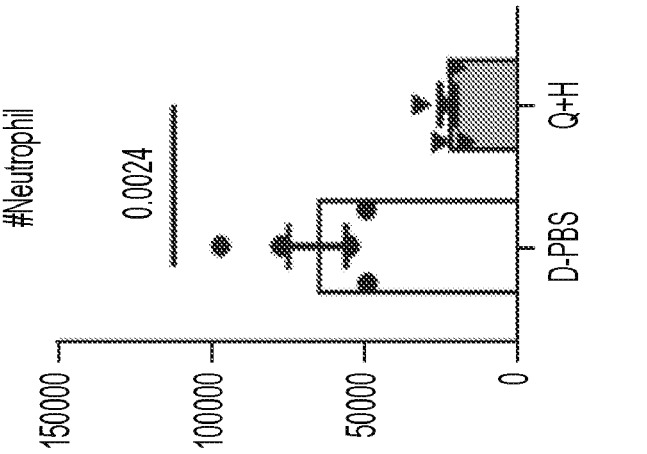
FIG. 16B
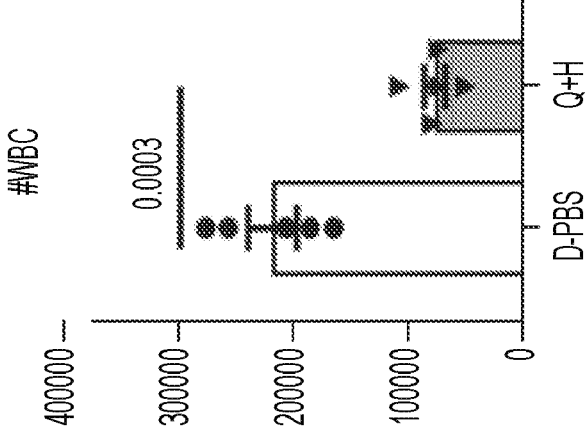

COMPOUNDS FOR TREATMENT OF HEMOLYSIS-AND INFLAMMASOME-ASSOCIATED DISEASES

CROSS-REFERENCE TO RELATED APPLICATIONS

The present application is a U.S. National Phase Application based on International Patent Application PCT/US2021/054827 filed Oct. 13, 2021, which claims priority under 35 U.S.C. § 119 (e) to U.S. Provisional Applications 63/091,140 filed Oct. 13, 2020 and 63/160,351 filed Mar. 12, 2021. Each of these applications is incorporated herein by reference in their entirety.

STATEMENT REGARDING FEDERALLY-SPONSORED RESEARCH

This invention was made with government support under Grant Nos. 5 R35 HL161239-04, 5 P01 HL149626-05 awarded by the National Institute of Health. The government has certain rights in the invention.

BACKGROUND

Hemolysis is a hallmark of sickle cell disease (SCD). When deoxygenated, sickle hemoglobin polymerizes, causing changes in RBC membrane shape and function that increase its fragility and ultimately lead to RBC destruction and hemoglobin release. Increasing evidence suggest that hemoglobin and its oxidized form of free heme, a lipophilic bioactive molecule, play a key role in the initiation and progression of hemolytic complications due to their ability to trigger oxidative stress, sterile inflammation, cell death and tissue injury.

The inflammasome signaling pathway is a key host inflammatory response that promotes IL-1β production by processing pro-IL-1β into cleaved mature IL-1β. It is activated in numerous inflammatory diseases and upregulate in SCD. inflammasome activation are critical for the initiation, development, treatment, and prognosis of multiple disease which include infectious diseases, autoimmune diseases, cancer, and metabolic disorder and other disease including SCD, and pharmacological inhibition of inflammasome pathway are considered as a promising therapeutic strategy in several inflammatory disease models (Guo H et al. Nat Med. 21:677-87, 2015; Mangan M S J, et al. Nat Rev Drug Discov. 17:588-606, 2018).

Quinine can bind with cell-free heme/hemin released by hemolysis and inhibit multiple immune effector cell function including secretion of antibodies by B cells and release of inflammatory cytokines by innate immune cells.

SUMMARY

Disclosed herein are methods of treating a complication of a hemolysis and/or inflammasome activation-associated disease comprising administering to a patient in need thereof a therapeutically effective dose of quinine alone or a combination of quinine and hemin. In some embodiments, the complication is induction of a humoral immune response to transfused red blood cells, inflammatory cytokine production, or pain.

Also disclosed is a method of reducing alloimmunization in chronically transfused subjects, comprising administering to a patient in need thereof a therapeutically effective dose of quinine. In some embodiments, the subject has a hemolysis-associated disease.

In some embodiments, the hemolysis-associated disease is sickle cell disease. In some embodiments, the inflammasome-associated disease is an infectious disease, autoimmune disease, cancer, metabolic disorder, or sickle cell disease. In some embodiments, the patient exhibits hemolysis. In some embodiments, the quinine alone or the combination of quinine and hemin inhibits the maturation of B cells into antibody-secreting cells.

In some embodiments, the method comprises administration of a therapeutically effective dose of quinine. In some embodiments, the method comprises administration of a therapeutically effective dose of a combination of quinine and hemin. In some embodiments, exogenous hemin is not administered.

In some embodiments, the quinine plus hemin inhibits inflammasome activation in innate immune cells leading to decreased inflammatory cytokine production. In some embodiments, the inhibition by quinine alone occurs in the presence of hemolysis or free heme in the blood. In some embodiments, the inhibition by quinine alone does not occur in the absence of hemolysis or free heme in the blood. In some embodiments, the inhibition by the combination of quinine and hemin does not depend on the presence of endogenous free heme in the blood. In some embodiments, the patient exhibits low or no in vivo hemolysis.

In some embodiments, the disease is an inflammasome-associate disease and the administration comprises quinine alone and exogenous hemin is not administrated.

In some embodiments, the quinine is a quinine salt. In some embodiments, the quinine is quinine free base. In some embodiments, the quinine is a quinine derivative selected from quinacrine, biquinoline, chloroquine, hydroxychloroquine, amodiaquine, quinine, quinidine, mefloquine, primaquine, lumefantrine, and halofantrine.

BRIEF DESCRIPTION OF THE DRAWINGS

FIG. 1A: Using the gating strategy for analysis of proliferated B cells and CD38+ plasmablasts, FIG. 1B: Frequency of proliferated B cells in total B cells and of CD38+ plasmablasts in the absence or presence of 2.5 μM heme is shown. FIG. 1C: Fold change in proliferated B cell and CD38+ plasmablast frequencies in the presence of increasing doses of heme relative to no heme treatment. FIG. 1D: Fold change in CD38+ plasmablast frequencies in the presence of different doses of RBC lysate or heme (left) or a given RBC lysate dose or 2.5 μM heme preincubated or not with 2.5 μM hemopexin (right). FIG. 1E: Cell-free heme levels just before transfusion or within 4 hours post-transfusion in plasma from Allo(+) and Allo(−) sickle cell disease (SCD) patients. FIG. 1F: CD38+ plasmablast frequencies in stimulated naïve B cells from HD, Allo(+) and Allo(−) SCD patients. FIG. 1G: Fold change in CD38+ plasmablast frequencies in the presence of 2.5 μM and 5 μM heme. p-values are labeled as * (p<0.05) or ** (p<0.01). HPX: Hemopexin.

FIG. 2A: Purified HD naïve B cells were stimulated with B cell activation cocktail, and phosphorylation of Pyk2, Syk, SRC and STAT3 were analyzed by intracellular flow cytometry after 15 mins. Histogram overlays depict the extent of phosphorylation without (light grey) or with stimulation (dark grey) with the phosphorylated signal gate placed by reference to the baseline, pre-stimulation histogram. FIG. 2B: Purified HD naïve B cells were stimulated for the same length of time as in A in the absence or presence of heme (10 μM) and the frequency of cells positive for p-Pyk2, p-Syk, p-SRC and p-STAT3 is shown. FIG. 2C: Purified HD naïve B cells were stimulated with B cell activation cocktail for 7 days. Contour plots depict gating strategy for DOCK8 LOW, DOCK8 HIGH in proliferated B cells as well as plasma B cells (CD27$^{hi}$Blimp1$^+$ cells) within DOCK8$^{lo}$ or DOCK8$^{hi}$ cells. FIG. 2D: Fold change in plasma B cell frequencies in 7-day purified HD naïve B cell stimulated cultures in the presence of 2.5 μM or 5 μM heme relative to no heme stimulated B cells. FIG. 2E: DOCK8$^{high}$ (left) and DOCK8$^{low}$ (middle) cell numbers in stimulated B cell cultures treated with 2.5 μM or 5 μM heme. Fold change (right) in DOCK8$^{hi}$ or DOCK8$^{lo}$ cell numbers with heme treatment relative to no treatment. FIG. 2F: Representative histogram (left) overlay showing DOCK8 expression (dark grey) in peripheral B cells relative to isotype control (light grey). Relative DOCK8 expression (mean fluorescence intensity; right) in circulating B cells from HD, Allo(−) and Allo(+) patients are shown. FIG. 2G: Fold change in DOCK8$^{hi}$ B cell (left) and CD27$^{hi}$ plasma cell (right) frequency in 7-day heme-treated cultures of stimulated naïve B cells from Allo(−) and Allo(+) patients.

FIG. 3A: HO-1 analysis of HD unstimulated peripheral blood B cells (left) and following 7-day stimulation of purified naïve B cells in proliferated B cells (gate showing CD38+ plasmablasts). FIG. 3B: Fold change in HO-1 expression in plasma cells in 7-day stimulated purified HD B cells treated 2.5 μM or 5 μM heme relative to no heme treatment. FIG. 3C-D: Absolute and fold change of frequency of B cell proliferation (FIG. 3C) and CD38+ plasmablasts (FIG. 3D) in the presence of SnPPIX (2.5 μM) without or with heme (2.5 μM). FIG. 3E: Fold change in B cell proliferation and plasma B cells 7-day stimulated naïve B cells from Allo(+) and Allo(−) SCD patients in the absence or presence of SnPPIX (2.5 μM) and heme (2.5 μM) relative to untreated media control. FIG. 3F: Fold change in B cell proliferation and plasma B cells 7-day stimulated HD naïve B cells in the presence of different doses of heme degradation byproducts, CORM-3 (carbon monoxide releasing molecule 3) and biliverdin relative to untreated cultures.

FIG. 4C: Levels of HO-1 expression (mean fluorescent intensity, MFI) in proliferated B cells of 7 day stimulated B cells treated with different doses of quinine without or with 5 μM heme. FIG. 4D: Fold change in HO-1 expression in stimulated B cells in the presence of 2.5 μM QA, AQ, CQ and DHA without or with 5 μM free heme relative to untreated but stimulated cultures. FIG. 4E: Fold change in plasma cell frequency in stimulated purified naïve B cells from Allo(+) and Allo(−) patients in the presence of different doses of quinine plus 2.5 μM or 5 μM heme. *: p<0.05 vs control group; **: p<0.001 vs control group.

Figure 5:
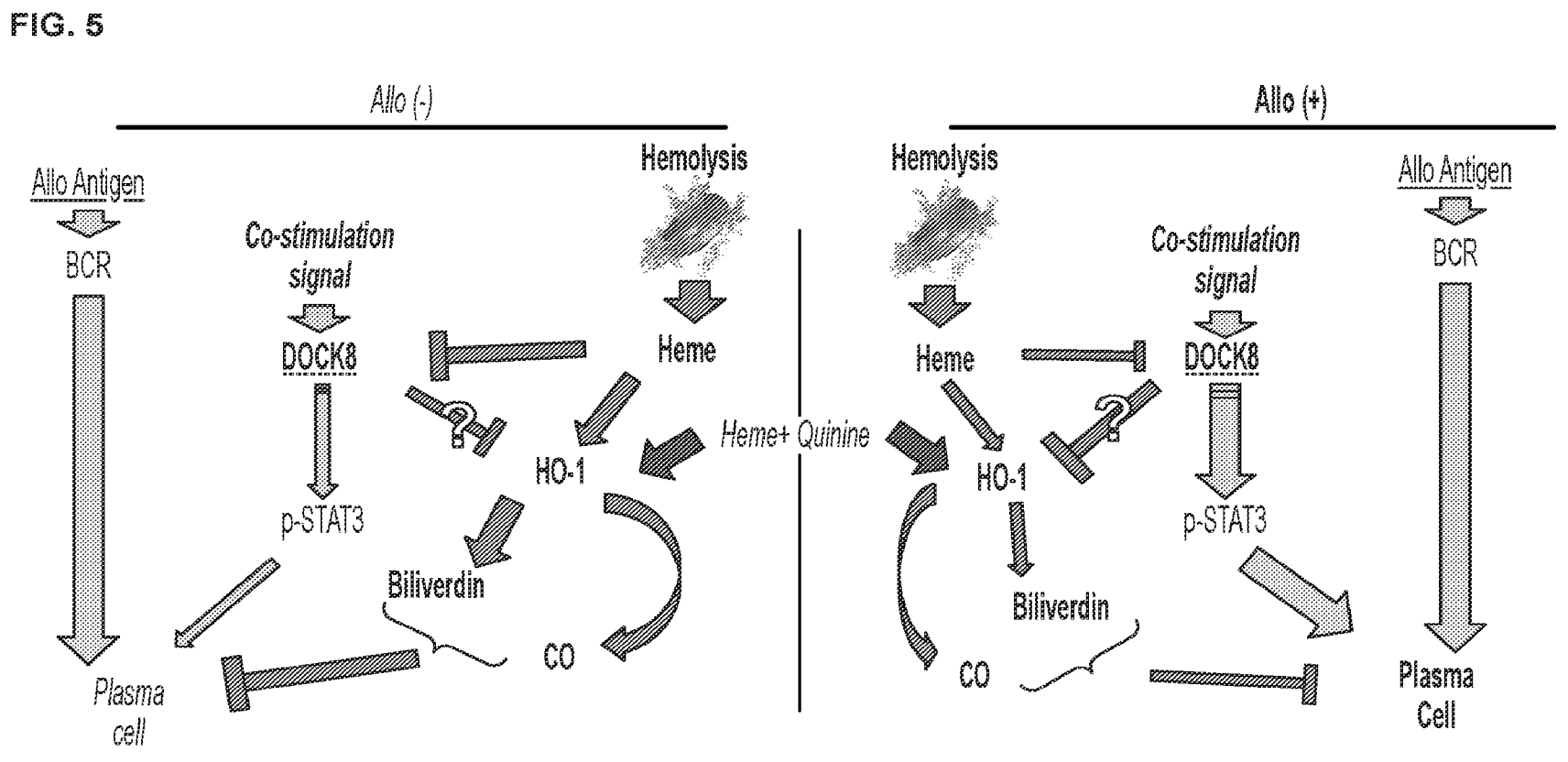

FIG. 5: Mechanism of hemolysis mediated regulation of SCD alloimmunization through inhibition of B cell differentiation. In Allo(−) SCD patients, hemolysis can inhibit B cell differentiation and subsequent alloimmunization through DOCK8 and HO-1 enzyme activity. In contrast, B cells from Allo(+) SCD patients are insensitive to inhibitory effects of hemolysis due to altered DOCK8 and HO-1 signaling pathways. Heme plus quinine can inhibit B cell activation in both Allo(+) and Allo(−) patients by targeting HO-1. BCR: B cell receptor; CO: carbon monoxide.

FIG. 6A: Gating strategy for single live B cell analysis after culture. FIG. 6B: Fold change in CD38+ plasmablast cells in 7-day stimulated HD purified CD27+ memory B cells (as described for naïve B cell cultures in FIG. 1) in the presence of different doses of hemin relative to no hemin treatment. FIG. 6C: Histogram showing IgG expression levels in CD38+ plasmablasts from naïve B cell stimulated cultures. FIG. 6D: Fold change of IgG+ cell frequency in CD38+ plasmablasts in the presence of 2.5 μM or 5 μM hemin relative to no hemin treatment in stimulated naïve B cells from HD, Allo(−) and Allo(+) SCD patients. FIG. 6E: Naïve B cells from HD were cultured with 20% SCD patients' sera from Allo(−) or Allo(+) patients and stimulated with B cell activation cocktail for 7 days as described. Frequency of CD38+ plasmablasts is shown. FIG. 6F: Fold change of proliferated B cell frequency (within total, live B cells) in the presence of 2.5 μM or 5 μM hemin relative to no hemin treatment in stimulated naïve B cells from HD, Allo(−) and Allo(+) SCD patients. FIG. 6G: The change and fold change of live cell frequency in total 7-day stimulated HD B cell in the presence of different concentrations of hemin.

FIG. 7A: Frequency of p-Pyk2, p-SRC, and p-SYK positive cells following stimulation of naïve HD B cells for 15, 30, 60 mins as described in FIG. 2A. FIG. 7B-left: Representative histogram overlays of p-STAT3 (light gray: isotype control; medium gray: without heme; dark gray: with heme) in overnight stimulated naïve HD B cells in the absence or presence of heme (10 μM). FIG. 7—right: Adjusted mean fluorescence intensity (MFI) to measure p-STAT levels without or with hemin. FIG. 7C: Relative DOCK8 levels (MFI) in circulating CD4+ T cells and monocytes from HD, Allo(−) and Allo(+) patients.

FIG. 8A: Frequency of CD38+ plasmablasts in 7-day stimulated HD naïve B cells (as in FIG. 1A) treated without and with 5 μM iron chelator deferoxamine (DFO) in the absence or presence of hemin (2.5 μM). FIG. 8B: Purified HD naïve B cells were stimulated with B cell activation cocktail for 7 days. Contour plots showed higher HO-1 expression in DOCK8hi B cells (left) and CD27hi expressing B cells (right).

FIG. 9A: Fold difference in DOCK8 expression relative to no treatment in proliferated B cells (as in FIG. 2C) following stimulation of purified HD naïve B cells for 7 days treated with different doses of quinine in the presence of 2.5 μM and 5 μM hemin. FIG. 9B: The frequency of live cells in the entire 7 day cultures in the presence of different doses of hemin and quinine.

and CpG (ODN1826) (1 μg/ml) without or with different doses of quinine and in the absence or presence of 2.5 μM or 5 μM concentration of hemin. Fold difference in proliferated B cells (FIG. 10A) and CD138+ plasma B cells (FIG. 10B) are shown. FIG. 10C: Representative experiment in SCD mice following transfusion of RBCs expressing human GPA (huGPA RBCs) collected from mice transgenic for human GPA in the absence or presence of quinine (QA). Briefly, mice were transfused twice with 100 ml of huGPA RBCs, each transfusion given one week apart. Mice were treated intraperitoneally twice per day with QA (12 mg/kg, reported to maintain serum quinine levels at 0.5~1 μM) or the same volume PBS. Levels of anti-GPA antibody in plasma were measured 7 days after the last transfusion by flow cytometry.

FIG. 13A-D depicts human monocytes isolated from peripheral blood were cultured with LPS for 3 hours to prime pro-IL-1β production followed by addition of various NLRP3 pathway agonists to trigger IL-1β secretion without or with therapeutic reagents including hemin, quinine or hemin plus quinine (all at 2.5 μM concentration for all experiments except the dose response studies in FIGS. 13B and C). Levels of IL-1β, IL-6 and TNF-α in the culture supernatants was analyzed 30 min (for ATP treatment) or 2 hours (for nigericin and imiquimod) after addition of NLRP3 agonists. FIG. 13A: The effect of hemin, quinine and hemin plus quinine on IL-1β secretion triggered by various NLRP3 agonists. FIG. 13B: The dose dependent effect of hemin, quinine and hemin plus quinine. FIG. 13C: The effect of QA, CQ, AQ, and DHA in the presence/absence of hemin. FIG. 13D: The effect of hemin, quinine, or hemin plus quinine on IL-6 and TNF-α.

FIG. 17A: SCD mice were I.P. injected with alum (700 μg/mice) along with D-PBS as control, hemin, quinine, or Q+H. Mice survival were monitored for 24 hours. FIG. 11B: The effects of hemin, quinine, Q+H on IL-1β were tested in monocytes from SCD patients treated with NLRP3 inflammasome agonists nigericin and imiquimod.

DETAILED DESCRIPTION

Figures 1A, 1B:
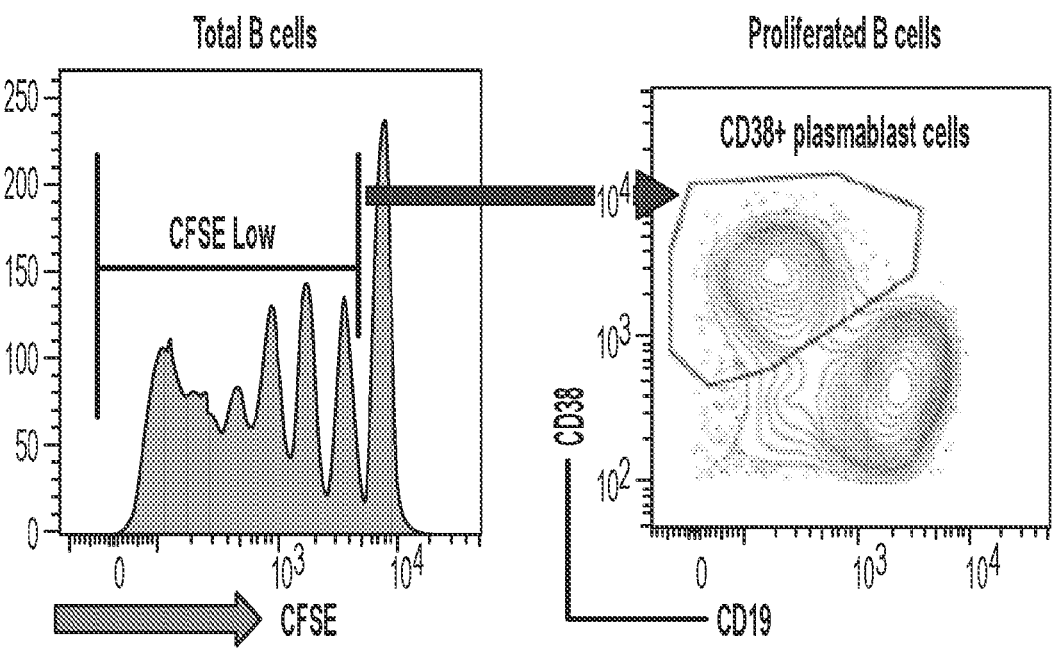
FIG. 1A-G. Heme inhibits B cell activation. Purified naïve B cells from healthy donors (HD) were CFSE labeled and stimulated with B cell activation cocktail for 7 days.

This disclosure is focused on hemolysis and inflammasome associated complications in sickle cell disease (SCD)

and other diseases with inflammasome activation. Disclosed herein is that cell-free heme/hemin released by hemolysis may modulate the risk, initiation and development of these complications including humoral immune responses to transfused red blood cell and pain crisis. By screening multiple heme-binding small molecules, it was determined that quinine showed strong biologic activities including inhibiting B cells maturating into antibody secreting cell (plasma cells) and innate immune cells secreting inflammatory cytokines in the presence of free heme or hemolysis but not in the absence of heme or hemolysis. These data indicate that through its ability to bind to heme, during hemolytic crises when there are high in vivo free heme levels, quinine alone could be used to inhibit detrimental antibody production, such as delayed hemolytic reactions after red cell transfusions, and prevent inflammatory cytokine secretion, such as during pain crisis. Quinine may also inhibit complications in other hemolytic diseases with overt intravascular hemolysis. Furthermore, a dose of an in vitro mixture of quinine plus heme is useful to inhibit detrimental antibodies and inflammatory cytokines production in the case of low or no in vivo hemolysis.

Hemolysis-associated diseases include any condition which causes lysis of red blood cells. Hemolysis inside the body can be caused by a large number of medical conditions, including infection by many Gram-positive bacteria (e.g., *Streptococcus, Enterococcus*, and *Staphylococcus*), infection by some parasites (e.g., *Plasmodium*), some autoimmune disorders (e.g., drug-induced hemolytic anemia, atypical hemolytic uremic syndrome (aHUS)), and some genetic disorders (e.g., sickle-cell disease or G6PD deficiency).

Inflammasome-associated diseases are inflammatory diseases in which inflammasome activation is critical for disease initiation, development, treatment, and/or prognosis. These diseases include infectious diseases, autoimmune diseases, cancer, metabolic disorder, and other diseases including SCD.

Sickle cell disease (SCD) is an inherited group of blood disorders. The most common type is known as sickle cell anemia. Sickle cell disease results from a mutation in the oxygen-carrying protein hemoglobin found in red blood cells leading to the red blood cells assuming a rigid, sickle-like shape under certain circumstances such as temperature changes, stress, dehydration, and high altitude. Symptoms of sickle cell disease typically begin around 5 to 6 months of age.

The loss of red blood cell elasticity is central to the pathophysiology of sickle cell disease. Normal red blood cells are quite elastic and have a biconcave disc shape, which allows the cells to deform to pass through capillaries. In sickle cell disease, low oxygen tension promotes red blood cell sickling and repeated episodes of sickling damage the cell membrane and decrease the cells elasticity. These cells fail to return to normal shape when normal oxygen tension is restored. As a consequence, these rigid blood cells are unable to deform as they pass through narrow capillaries, leading to vessel occlusion and ischemia. The actual anemia of the illness is caused by hemolysis, the destruction of the red cells, because of their shape. Although the bone marrow attempts to compensate by creating new red cells, it does not match the rate of destruction. Healthy red blood cells typically function for 90-120 days, but sickled cells only last 10-20 days. A hemolytic crisis occurs when there is an acute accelerated drop in the hemoglobin level due to the breakdown of red blood cells.

Blood, and/or red cell, transfusions are used for prevention of complications associated with SCD by decreasing the concentration of sickle hemoglobin in the blood. Some patients receive transfusions every two to four weeks for their entire life. However, chronic transfusion therapy also has side effects including alloimmunization (development of antibodies to the donor's red blood cells) despite rigorous blood group typing and matching, and iron overload (treated by chelation therapy). Complications of hemolysis-associated diseases include induction of a humoral immune response to transfused red blood cells, inflammatory cytokine production, and pain.

In subjects with sickle cell disease, or a related disorder, physiological changes in RBCs can result in a disease with the following signs: (1) hemolytic anemia: (2) vaso-occlusive crisis; and (3) multiple organ damage from microinfarcts, including heart, skeleton, spleen, and central nervous system.

SCD is a form of hemolytic anemia, with red cell survival of around 10-20 days. Approximately one third of the hemolysis occurs intravascularly, releasing free hemoglobin (plasma free hemoglobin [PFH]) and arginase into plasma. PFH has been associated with endothelial injury including scavenging nitric oxide (NO), proinflammatory stress, and coagulopathy, resulting in vasomotor instability and proliferative vasculopathy. A hallmark of this proliferative vasculopathy is the development of pulmonary hypertension in adulthood.

Vaso-occlusive crisis occurs when the circulation of blood vessels is obstructed by sickled red blood cells, causing ischemic injuries. The most common complaint is of pain, and recurrent episodes may cause irreversible organ damage. One of the most severe forms is the acute chest syndrome which occurs as a result of infarction of the lung parenchyma. Vaso-occlusive crisis can be accompanied by a pain crisis which can occur suddenly and last several hours to several days.

The pain can affect any body part. It often involves the abdomen, bones, joints, and soft tissue, and it may present as dactylitis (bilateral painful and swollen hands and/or feet in children), acute joint necrosis or avascular necrosis, or acute abdomen. With repeated episodes in the spleen, infarctions and autosplenectomy predisposing to life-threatening infection are usual. The liver also may infarct and progress to failure with time. Papillary necrosis is a common renal manifestation of vaso-occlusion, leading to isosthenuria (i.e, inability to concentrate urine).

Severe deep pain is present in the extremities, involving long bones. Abdominal pain can be severe, resembling acute abdomen; it may result from referred pain from other sites or intra-abdominal solid organ or soft tissue infarction. Reactive ileus leads to intestinal distention and pain.

Bone pain and abdominal pain may be present. The face also may be involved. Pain may be accompanied by fever, malaise, and leukocytosis.

Skeletal manifestations include, but are not limited to, infarction of bone and bone marrow, compensatory bone marrow hyperplasia, secondary osteomyelitis, secondary growth defects, intravascular thrombosis, osteonecrosis (avascular necrosis/aseptic necrosis), degenerative bone and joint destruction, osteolysis (in acute infarction), articular disintegration, myelosclerosis, periosteal reaction (unusual in the adult), H vertebrae (steplike endplate depression also known as the Reynold sign or codfish vertebrae), dystrophic medullary calcification, bone-within-bone appearance, decreased density of the skull, decreased thickness of outer table of skull due to widening of diploe, hair on-end striations of the calvaria, osteoporosis sometimes leading to biconcave vertebrae, coarsening of trabeculae in long and flat bones, and pathologic fractures, bone shortening (premature epiphyseal fusion), epiphyseal deformity with cupped metaphysis, peg-in-hole defect of distal femur, and decreased height of vertebrae (short stature and kyphoscoliosis).

Renal manifestations include, but are not limited to, various functional abnormalities such as hematuria, proximal tubule dysfunction, impaired potassium excretion, and hyperkalemia; and gross anatomic alterations, for example, hypertrophied kidneys, with a characteristic smooth, capsular surface.

Splenic manifestations include, but are not limited to, enlargement, including rapid and/or painful enlargement known as splenic sequestration crisis, infarction, low pH and low oxygen tension in the sinusoids and splenic cords, functional impairment, autosplenectomy (fibrosis and shrinking of the spleen in advanced cases), immune deficiency and increased risk of sepsis.

Other common symptoms include lower serum immunoglobulin M (IgM) levels, impaired opsonization, and sluggish alternative complement pathway activation, increase susceptibility to infection pneumonia, bronchitis, cholecystitis, pyelonephritis, cystitis, osteomyelitis, meningitis, and sepsis and other challenges from infectious agents including, but not limited to, *Mycoplasma pneumoniae, Salmonella typhimurium, Staphylococcus aureus*, and *Escherichia coli*; growth delays or maturation delays during puberty in adolescents, hand-foot syndrome, acute chest syndrome, stroke, hemiparesis, hemosiderin deposition in the myocardium, dilation of both ventricles and the left atrium, cholelithiasis, paraorbital facial infarction, retinal vascular changes, proliferative retinitis, loss of vision, leg ulcers, priapism, avascular necrosis, and pulmonary hypertension.

Red blood cell alloimmunization remains a barrier for safe and effective transfusions in SCD, but all the associated risk factors remain largely unknown. Intravascular hemolysis, a hallmark of SCD, results in the release of heme with potent immunomodulatory activity, although its effect on SCD humoral response, specifically alloimmunization, remains unclear. Cell-free heme suppresses human B cell plasmablast/plasma cell differentiation by inhibiting the DOCK8/STAT3 signaling pathway, which is critical for B cell activation, as well as by upregulating heme oxygenase 1 (HO-1) through its enzymatic byproducts, carbon monoxide and biliverdin. Whereas non-alloimmunized SCD B cells are inhibited by exogenous heme, B cells from the alloimmunized group are non-responsive to heme inhibition and readily differentiate into plasma cells. Consistent with a differential B cell response to hemolysis, elevated B cell basal levels of DOCK8 and higher HO-1-mediated inhibition of activated B cells is seen in non-alloimmunized compared to alloimmunized SCD patients. To overcome the alloimmunized B cell heme insensitivity, we screened several heme-binding molecules and identified quinine as a potent inhibitor of B cell activity, reversing the resistance to heme suppression in alloimmunized patients. B cell inhibition by quinine only occurs in the presence of heme and through HO-1 induction. Thus, hemolysis can dampen the humoral B cell response and B cell heme responsiveness may be a determinant of alloimmunization risk in SCD. Quinine, by restoring B cell heme sensitivity, has therapeutic potential to prevent and inhibit alloimmunization in SCD patients.

Differential innate immune control of T cells skews between non-alloimmunized and alloimmunized SCD patients under hemolytic conditions, in part due to differences in monocyte levels of HO-1, an immunoregulatory enzyme with anti-cytotoxic, and anti-inflammatory properties. Differences in heme-mediated NFκb activation and maturation of $T_H1$ polarizing dendritic cells are found between alloimmunized and non-alloimmunized SCD patients. However, direct effects of hemolysis on human humoral immune cell response and RBC alloimmunization remain largely unknown. With respect to the effects on B cells, a study in mice (Watanabe-Matsui M. et al. *Blood.* 2011:117:5438-5448) showed that heme increases plasma B cell differentiation and IgM production through binding and induction of Bach2 degradation. In addition, mitochondrial-derived reactive oxygen species (ROS) inhibit mouse plasma cell differentiation by reducing endogenous heme synthesis. However, the effect of heme on human B cells has not yet been studied. Src-Syk-Stat3 activation through DOCK8, an adaptor protein that binds to free heme, is important for B cell activation and function. Interestingly, DOCK8-deficiency is associated with impairment of memory B cell and margin zone B cell development. Free heme, through binding to DOCK8, may inhibit B cell activation and that differential heme signaling in B cells via STAT3 may dictate whether humoral immunity against transfused cells is aborted (non-alloimmunized) or induced (alloimmunized).

Thus, disclosed herein is the use of heme and heme-binding molecules in the reduction of alloimmunization and resultant sequelae in patients with a hemolysis-associated disease. In some embodiments, the hemolysis-associated disease is a sickle cell disease. Exemplary heme-binding molecules include, but are not limited to, quinine and quinine derivatives.

Quinine ((R)-(6-Methoxyquinolin-4-yl)[(1S,2S,4S,5R)-5-vinylquinuclidin-2-yl]methanol) is an antiprotozoal and an antimyotonic, and is known for the treatment of malaria caused by *Plasmodium* species, the treatment and prophylaxis of nocturnal recumbency leg muscle cramps, and the treatment of babesiosis caused by *Babesia microti*. Quinine is structurally similar to quinidine, which is also an antiprotozoal, but can function as an antiarrhythmic. Quinidine has been associated with the prolongation of the QT interval in a dose-related fashion. Excessive QT prolongation has been associated with an increased risk of ventricular arrhythmia. Although quinine is a diastereomer of quinidine, it does not cause QT prolongation to the same degree although it has been suggested that patients with a history of cardiac arrhythmias and/or QT prolongation should carefully consider taking quinine as they may be at risk for arrhythmias.

"Pharmaceutically acceptable salts" include derivatives of the active agent (e.g. quinine), wherein the parent compound is modified by making acid or base addition salts thereof. Also included are all crystalline, amorphous, and polymorph forms. Examples of pharmaceutically acceptable salts include, but are not limited to, mineral or organic acid addition salts; and the like. The pharmaceutically acceptable salts include salts, for example, from inorganic or organic acids. For example, acid salts include those derived from inorganic acids such as hydrochloric, hydrobromic, sulfuric, sulfamic, phosphoric, nitric and the like. Pharmaceutically acceptable organic salts includes salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like. Specific quinine salts include quinine sulfate, quinine hydrochloride, quinine dihydrochloride, and hydrates or solvates thereof. As used herein, the term "quinine" includes quinine salts. The term "quinine derivative" includes any chemical derivative of quinine and includes, but is not limited to, quinacrine, biquinoline, chloroquine, hydroxychloroquine, amodiaquine, quinine, quinidine, mefloquine, primaquine, lumefantrine, and halofantrine.

In some embodiments, quinine includes a pharmaceutically acceptable solvate, including hydrates of such compounds and salts thereof.

Hemin is an iron-containing porphyrin (iron(III) complex of protoporphyrin IX) which is administered intravenously for treatment of certain blood disorders. Hemin is also referred to as hematin.

The term "effective amount" or "therapeutically effective amount" means an amount effective, when administered to a patient, to provide any therapeutic benefit. A therapeutic benefit may be an amelioration of symptoms, e.g., an amount effective to decrease the severity, duration, response to treatment, or incidence of one or more of the symptoms disclosed herein.

The amount that is "effective" will vary from subject to subject, depending on the age and general condition of the individual, weight of the individual, including mass or surface area, the particular active agent, and the like. Thus, it is not always possible to specify an exact "effective amount." However, an appropriate "effective" amount in any individual case may be determined by one of ordinary skill in the art using routine experimentation. In certain circumstances a patient may not present symptoms of a condition for which the patient is being treated. A therapeutically effective amount of an active agent may also be an amount sufficient to provide a significant positive effect on any indicium of a disease, disorder, or condition, e.g. an amount sufficient to significantly reduce the severity of a SCD, or the risk or frequency of a pain or vaso-occlusive crisis. A significant effect on an indicium of a disease, disorder, or condition is statistically significant in a standard parametric test of statistical significance. In some embodiments, a therapeutically effective amount of quinine is a dose of 2-10 mg/kg twice daily. In some embodiments, the dose of quinine is 5 mg/kg. In some embodiments, the dose is 324 mg twice a day. In some embodiments, the patient does not have heart failure, myasthenia gravis, optic neuritis, or a known hypersensitivity to quinine, mefloquine, or quinidine.

Quinine dosage forms existing as liquids, solutions, emulsions, or suspensions can be packaged in a container for convenient dosing of pediatric or geriatric patients. For example, prefilled droppers (such as eye droppers or the like), prefilled syringes, and similar containers housing the liquid, solution, emulsion, or suspension form are contemplated.

In some embodiments, the methods disclosed herein comprises administration of a combination or quinine, or a salt or derivative thereof, and hemin. As used herein, the term "combination" refers to administration of both compounds and does not limit the administration to a single formulation that contains both quinine, or a salt or derivative thereof. In some embodiments, quinine is administered orally and hemin is administered intravenously. The two components of the combination may be, but are not necessarily, administered at the same time or on the same schedule. However, they should be administered in sufficient proximity in time that both components are present together in the body.

Also disclosed herein are inhibiting plasma cell differentiation comprising administration of a combination of quinine, or a derivative or salt thereof, and hemin. In additional embodiments, disclosed herein are methods of inducing expression of HO-1 comprising administration of a combination of quinine, or a derivative or salt thereof, and hemin.

EXAMPLES

Example 1. Hemolysis Inhibits Humoral B Cell Responses and Modulates Alloimmunization Risk in Patients with Sickle Cell Disease Materials and Methods:

Human samples. All studies were approved by the institutional Review Boards of the New York Blood Center (NYBC) and Montefiore Health Center. Our cohort of SCD patients (n=24, median age:18 years, range 13-36; 33% (n=8) females) were on a chronic red cell transfusion therapy (every 3-4 weeks for at least two years using leukodepleted units, phenotype matched for C, E and K red cell antigens), were all infectious-free at the time of blood sampling (Table 1) and stable with no recorded inflammatory SCD complications at the time of the blood draw for the study. Patients were grouped either as Allo(−) (n=12), having had no history of antibody production or Allo(+) (n=12) with a history of having produced at least one alloantibody. Of the 12 Allo(+) patients, 5 patients had detectable alloantibodies at the time of the blood draw. The blood samples from SCD patients were processed within 18 hours after collection. For circulating DOCK8 expression studies in healthy controls, peripheral blood samples from de-identified, race-matched healthy donors were used. Leukocyte enriched products from de-identified healthy donors were used for purification of B cells for in vitro culture studies.

Antibodies and Reagents. Antibodies were purchased from commercial sources: anti-human CD19 (PE-Cy7, Cat #:552854, BD Bioscience), anti-human CD38 (BV786, Cat #:563964, BD Bioscience), anti-human CD27 (BV711, Cat #:564893, BD Bioscience), anti-human IgG (BV421, Cat #:562581. BD Bioscience), anti-human Blimp-1 (PE. Cat #: 564702, BD Bioscience), anti-Pyk2 (pY402) (Alexa647, Cat #560256, BD Bioscience), anti-Src (pY418) (PE, Cat #560094, BD Bioscience), Anti-ZAP70 (PY319)/Syk (PY352) (Alexa647, Cat #:557817, BD Bioscience), anti-STAT3 Phospho (Tyr705) (Alexa 647, Cat #651008, Biolegend), anti-human HO-1 (Cat #: MA1-112, Thermo Fisher Scientific). The anti-human HO-1 antibody was conjugated with APC using Lightning-Link® APC Antibody Labeling Kit (NOVUS Biologicals). Other reagents purchased included hemin (Frontier Scientific), tin protoporphyrin IX (SnPPIX. Frontier Scientific), carbon monoxide releasing molecule-3 (CORM-3, Millipore-Sigma), biliverdin (Millipore-Sigma), quinine (Millipore-Sigma), chloroquine (Millipore-Sigma), amodiaquine (Millipore-Sigma), dihydroartemisinin (DHA, Millipore-Sigma). Syk Inhibitor II (Millipore-Sigma).

Hemin and RBC lysate preparation. Hemin, dissolved in dimethyl sulfoxide (DMSO), stock concentration 10 mM, was diluted to 100 μM with serum-free RPMI 1640 culture medium just prior to addition to B cell cultures. For short-term experiments lasting less than 24 hr, a final concentration of 10 μM hemin was used whereas for longer-term culture up to 7 days, 2.5-5 μM final heme concentration was used. RBC lysates were freshly prepared (containing ~80 g/L hemoglobin) for same day use. Briefly, 4 ml whole blood from healthy donors was passed through Acrodisc WBC syringe filter (Pall Corporation) to remove white blood cells followed by two washes with Dulbecco's Phosphate Buffered Saline (D-PBS) (200×g, 10 min at room temperature with no brake) for removal of platelets. The RBC pellet was lysed with 3 times volume of distilled water for 10 min at 37° C. Cellular debris was pelleted by centrifugation at 4000×g for 10 min at 4° C. The RBC lysate was transferred to a new tube and ⅑ volume of 10×D-PBS added. Prior to addition to the B cell cultures, the lysate was diluted with no serum RPMI 1640 using a final concentration of hemoglobin as ~2 g/L (high dose), the highest B cell tolerating dose that did not induce cytotoxicity, or ~1 g/L (low dose).

Cell isolation and culture. Peripheral blood mononuclear cells (PBMCs) were prepared by Ficoll (GE Healthcare) density gradient centrifugation from healthy donor leukopak products as well as from sickle peripheral blood apheresis waste bags. Human naïve and memory B cells were isolated from PBMCs using a human memory B Cell Isolation Kit (Miltenyi Biotec) by collecting CD27− B cells (naïve B cells) and CD27+ B cell (memory B cells) separately. The purity of naïve and memory B cells, as measured by flow cytometry, was about 95% (93-98%). RPMI 1640 culture medium was used for all cell culture experiments (supplemented with 10% FBS, 100-unit penicillin-streptomycin, 10 μM HEPES, 1 mM sodium pyruvate, all from Thermo Fisher Scientific). Purified B cells were stained with CFSE (Cat #: C34554, Thermo Fisher Scientific) and cultured in U-bottom 96 well plates (2.5×10⁵/well/200 μl culture medium) in the presence of goat anti-human IgA+IgG+IgM (H+L) F(ab')₂ fragment (2.5 μg/ml, Jackson ImmunoResearch), CD154 (10 ng/ml, R&D Systems) and CpG (ODN 7909, 1 nM, Cat #: tlrl-2006-1) without IL-2 for analysis of only CD38+ plasmablast differentiation or with IL-2 (5 ng/ml, Cat #:1081-IL-020, R&D Systems) in experiments to detect CD27$^{hi}$Blimp-1+ plasma cells. In addition, heme and various inhibitors were added to the cultures at the start point and incubated for 7 days.

Hemopexin neutralization. Hemopexin (stock concentration 500 μM, low endotoxin, Athens Research) was diluted to 25 μM with no serum RPMI 1640 and mixed with RBC lysate (hemoglobin ~10 g/L) or free hemin (25 μM) followed by incubation at 37° C. for 30 min. The same concentration of RBC lysate or free hemin was also incubated at 37° C. for 30 min as control. After 30 min, these were immediately added to B cells equivalent to ⅒ volume of the cultures for 7 days.

Plasma sample preparation and cell free heme analysis. Whole blood was centrifuged for 10 min at 200×g at room temperature with acceleration 1 and deceleration 0 and the separated plasma was re-centrifuged twice, first at 1200×g for 15 min and then 2500×g for 10 min, both times at room temperature and with no breaks on to remove platelets. The platelet free plasma was aliquoted and kept at −80° C. Heme concentration was analyzed using QuantiChrom™ Heme Assay Kit (BioAssay Systems) following the manufacturer's instructions.

Flow Cytometric Analysis

Cultured cells: stimulated B cells were transferred into U bottom 96 well plate and washed with 200 μl MACS buffer (D-PBS containing 0.5% BSA and 2 mM EDTA) at 300×g for 5 min at 4° C. After one wash, cells were stained for surface expression of CD19, CD38, CD27 using 25 μl staining buffer (anti-CD19, CD38, CD27 antibodies, diluted 200 fold with MACS buffer) for 30 min at 4° C. After one wash with 200 μl MACS buffer, cells were resuspended in 100 μl D-PBS and 50 μl Fixable Viability Dye eFluor™ 780 (1000 fold diluted with D-PBS, Thermo Fisher Scientific)

was added for dead cell detection for 5 min at room temperature. Cells were washed one time with MACS buffer and 100 µl D-DPS was added just before flow cytometric analysis (LSRFortessa flow cytometer, BD Bioscience). For intracellular staining of IgG, Blimp-1 and HO-1, samples were first washed with 200 µl MACS buffer before addition of 150 µl Fixation/Permeabilization buffer (Thermo Fisher Scientific) for 45 min at 4° C. After fixation, samples were washed twice with 1× Permeabilization buffer (Thermo Fisher Scientific) and stained with 25 µl intracellular staining buffer (anti-human IgG, DOCK8, Blimp-1, HO-1 antibodies, diluted 200 fold with 1× Permeabilization buffer) for 45 min at 4° C., after which the cells were washed twice with Permeabilization buffer and 100p D-DPS was added prior to flow cytometric analysis.

Protein phosphorylation analysis: B cells were short-term (maximum overnight) stimulated using the same B cell activation cocktail as above in the absence or presence of hemin (10 µM) after which B cells were fixed with the same volume pre-warmed Phosflow Fix buffer I (BD Bioscience) for 10 min at 37° C. After that, cells were washed twice with MACS buffer (400×g, 4° C., 5 min) followed by addition of 0.4 ml Perm buffer Ill (pre-chilled in −20° C., BD Bioscience) for 30 min on ice. After two washes with MACS buffer, samples were stained with staining buffer (anti-Pyk2 (pY402), SYK(pY319), SRC(pY418), and STAT3(pY705), 100 fold diluted with MACS buffer) at 4° C. for 45 min, washed and analyzed by flow cytometry.

Intracellular DOCK8 and HO-1 expression analysis in peripheral blood: peripheral blood samples, collected from healthy donors and SCD patients (just before RBC transfusion), were first stained (100 µl) with fluorescently conjugated anti-CD19 and CD27 antibodies ($\frac{1}{100}$ volume) for 30 min at room temperature prior to lysis with 3 ml RBC lysing buffer (BD Bioscience) at room temperature for 8 min. After washes with MACS buffer (300×g, 4° C., 5 min), the cells were fixed with 400 µl Fixation/Permeabilization buffer for 45 min at 4° C., after which the samples were washed twice with 2 ml 1× Permeabilization buffer and mixed with 50 µl intracellular staining buffer (anti-DOCK8 antibody, $\frac{1}{100}$ volume, and anti-HO-1 antibody, $\frac{1}{200}$ volume, in 1× Permeabilization buffer) for 45 min at 4° C. followed by washes and analysis by flow cytometry (LSRFortessa flow cytometer).

Statistical analysis. Data are represented as mean values±SEM. GraphPad Prism (GraphPad Software) was used for statistical analysis and figure presentation. Two-tailed Student's t-test (paired or unpaired) was used to determinate statistical significance, and p values<0.05 were considered as statistically significant.

Results

Figure 1C:
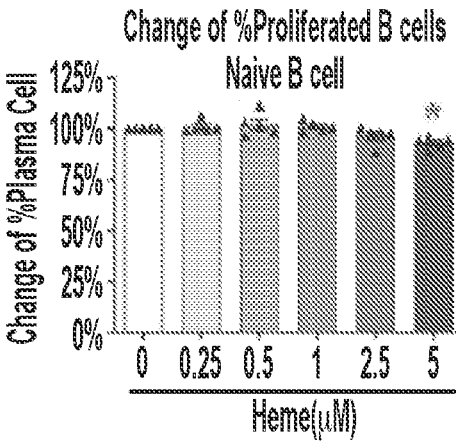
Figure 1C:
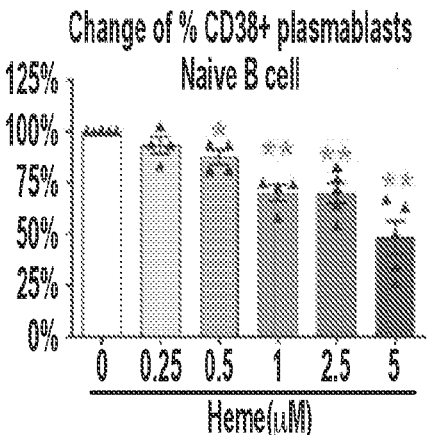
Figure 6A:
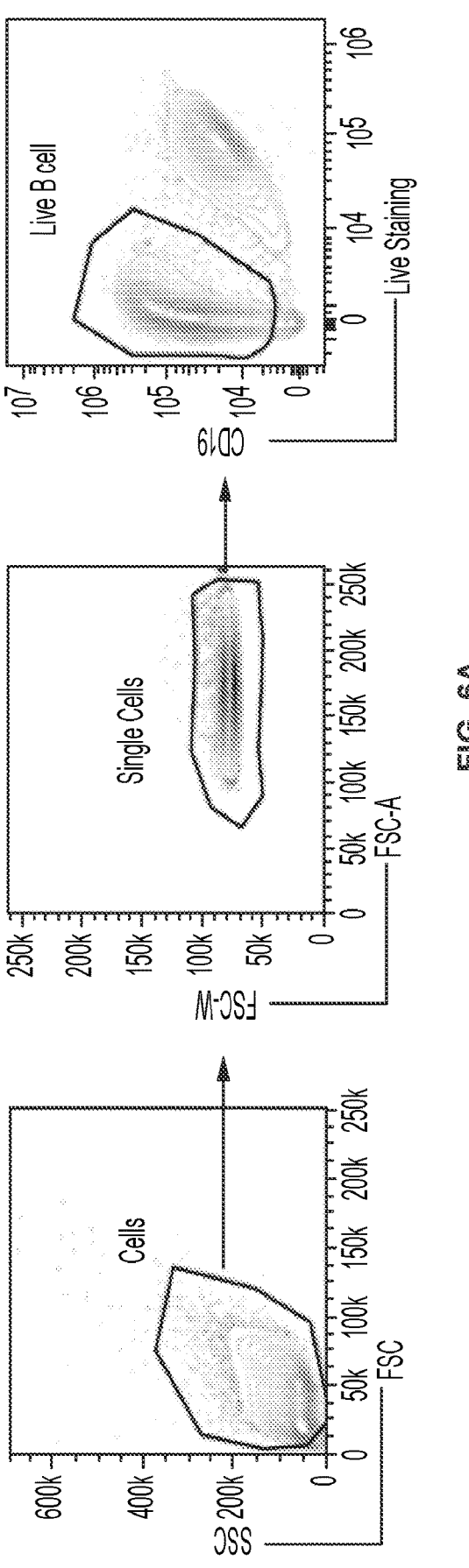
FIG. 6A-G. Effect of heme on memory plasmablast differentiation and IgG class-switch B cell development.
Figure 6C:
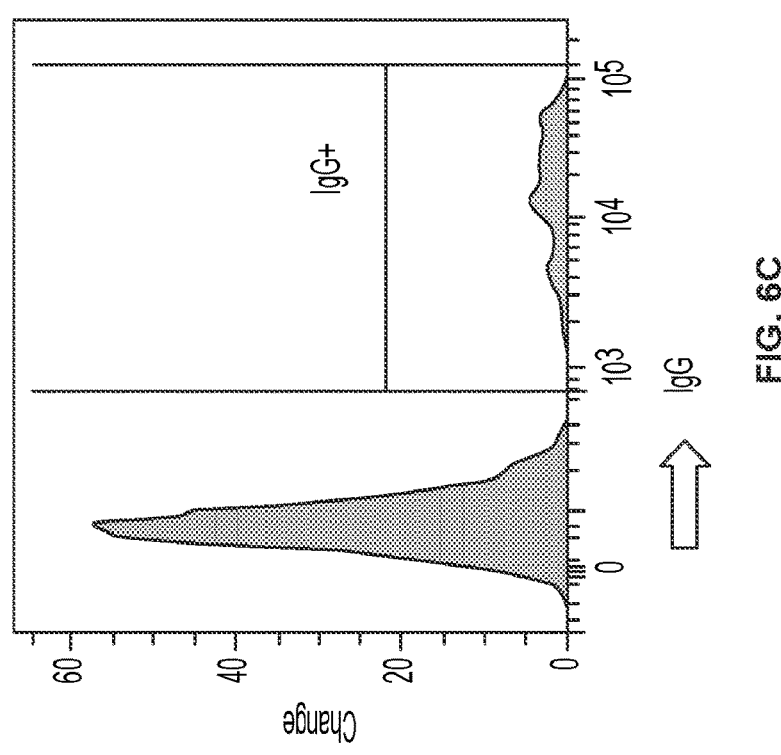
Figure 6B:
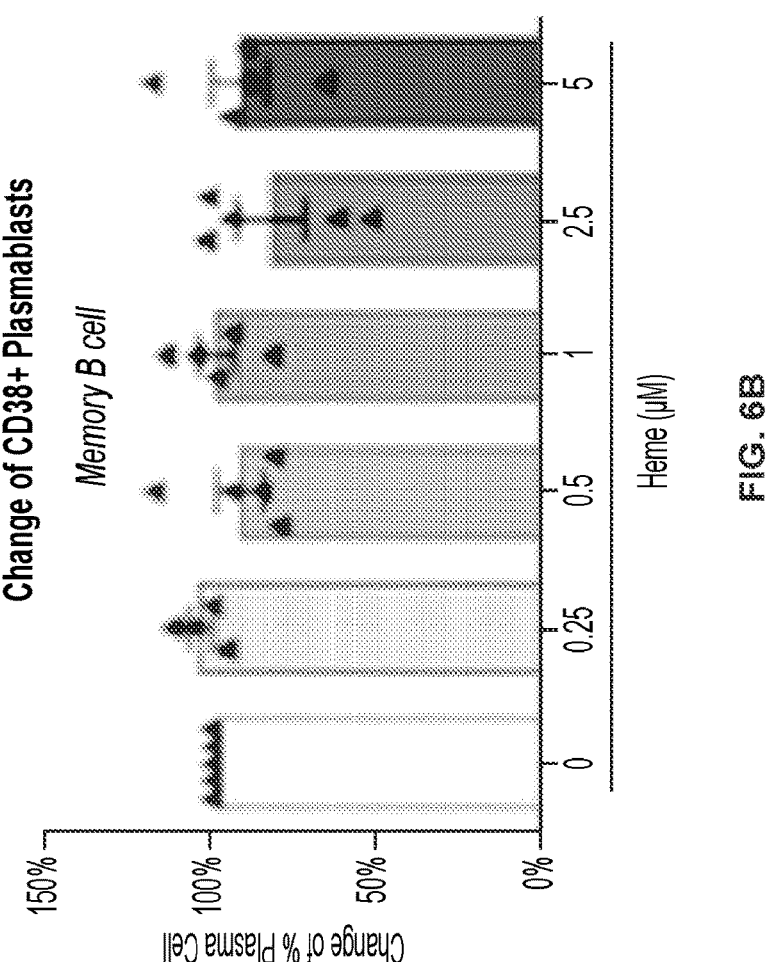
Figure 6E:
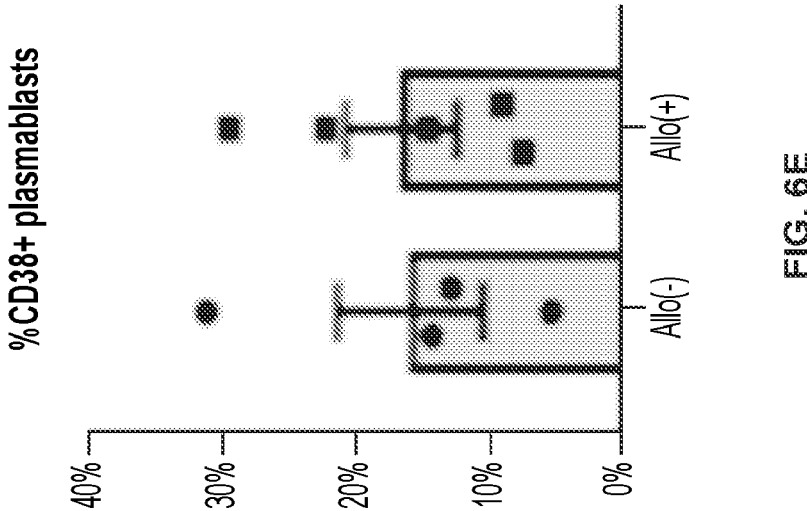
Figure 6D:
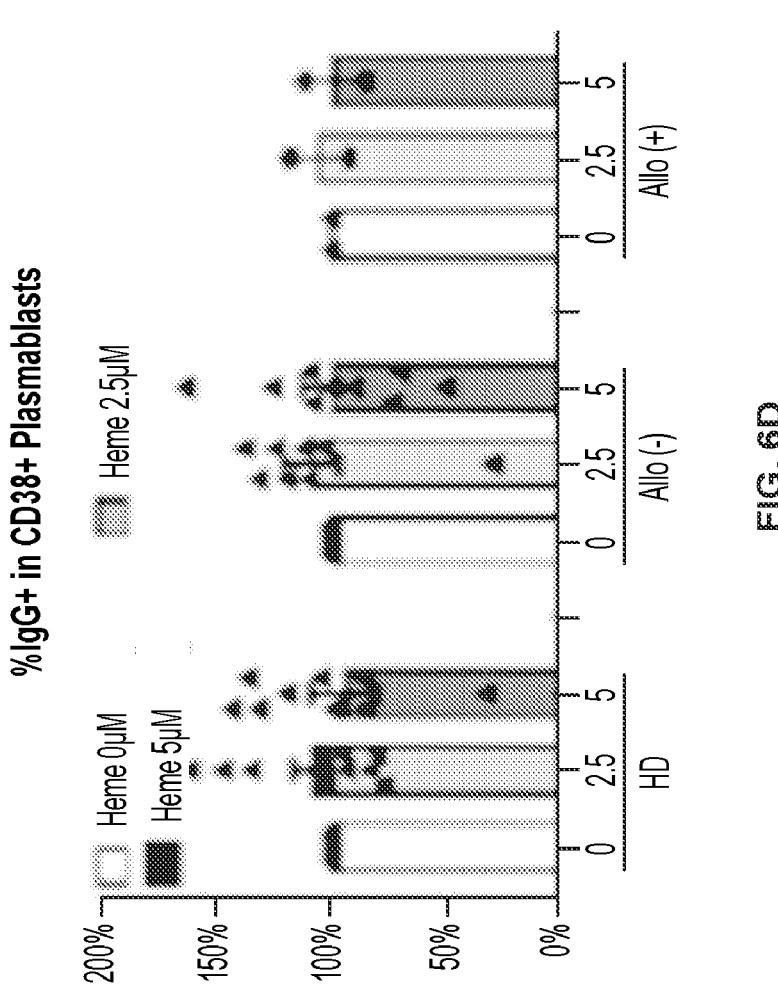
Figures 6F, 6G:
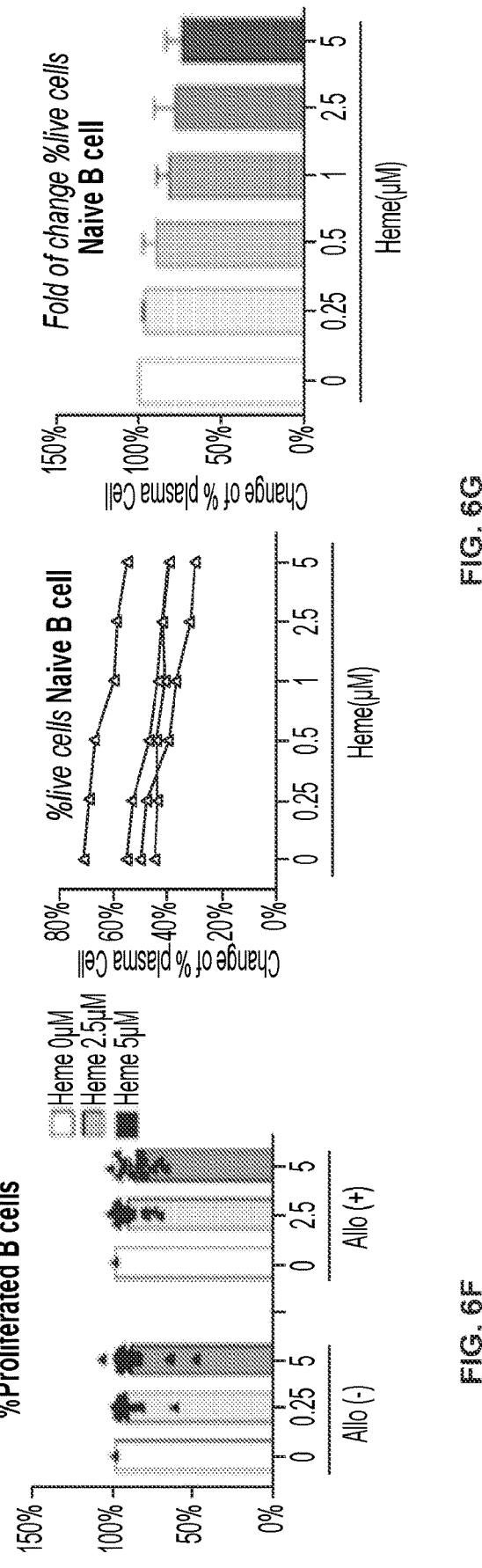

Hemolysis inhibits plasmablast cell differentiation. To test the effect of free heme on human B cell activation, purified circulating naïve (CD27⁻) and memory B cells (CD27⁺) from HDs, labeled with CFSE, were subjected to polyclonal activation to induce antigen-independent differentiation into antibody secreting cells, in the absence or presence of cell-free heme. After 7 days, the extent of proliferated (CFSE$^{low}$) CD19⁺ B cells and plasmablast differentiation (CD19$^{low}$CD38$^{hi}$) including IgG⁺ isotype switched B cells (CD19$^{low}$CD38$^{hi}$IgG⁺) within live B cells (FIG. 6A) was measured by flow cytometry (FIG. 1A and FIG. 6C). Based on our previous study in monocytes, the effect of 2.5 µM heme was tested first. In contrast to a minor inhibition of B cell proliferation, exogenous heme had a robust inhibitory effect on differentiation of naïve B cells into plasmablasts (FIG. 1B, p=0.0016). The inhibitory effect was dose-dependent, with 6.8%±1.3% inhibition of B cell proliferation and 52.7%±8.0% inhibition of plasmablast cell differentiation at the highest concentration tested (5 µM) (FIG. 1C). Interestingly, heme had no effect on memory B cell proliferation or differentiation (FIG. 6B). Similarly, B cell class switch recombination, measured as percent IgG⁺ B cells in proliferated B cells and plasmablast cells, was not affected by heme (FIG. 6C-D). The B cell analysis was restricted to live cells only and that even at the highest dose of heme used, the percentage of viable B cells were high (FIG. 6G).

Figure 1D:
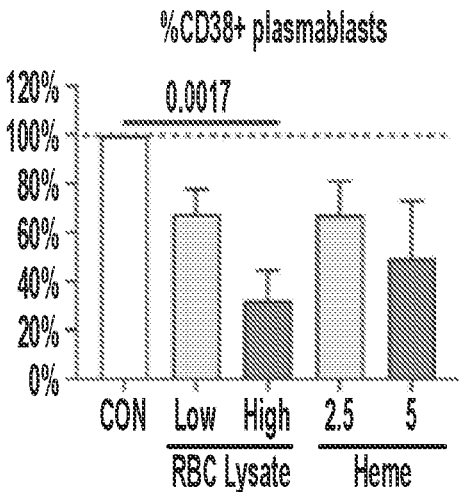
Figure 1D:
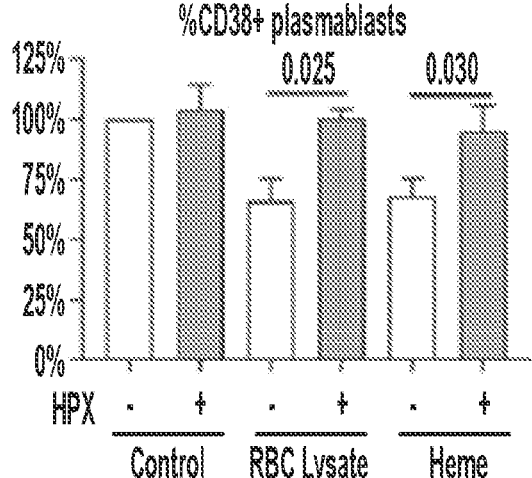

RBC lysates also induced a similar inhibition of plasmablast differentiation (FIG. 1D, p=0.0017). Pre-incubation of RBC lysate (1 g/L hemoglobin) or free heme (2.5 µM) with hemopexin (a heme scavenging protein, 2.5 µM) reversed the inhibitory effect (FIG. 1D), further confirming that inhibition was specific to heme. Altogether, these data suggest that plasma free heme inhibits naïve B cell activation predominantly at the plasmablast B cell differentiation stage.

Altered B Cell Home Response in Alloimmunized Patients with SCD.

Figure 1E:
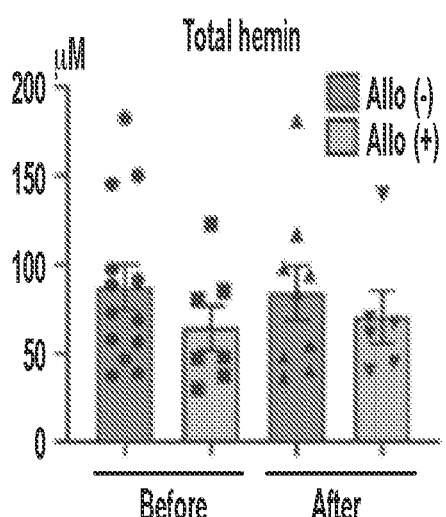
Figure 1F:
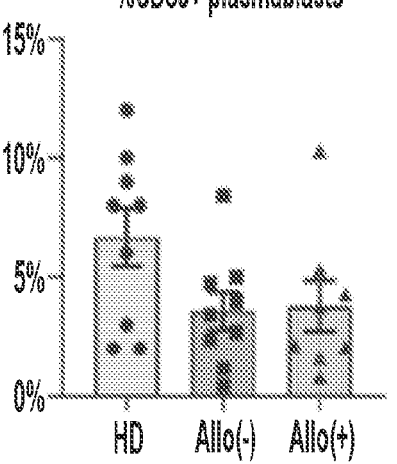
Figure 1G:
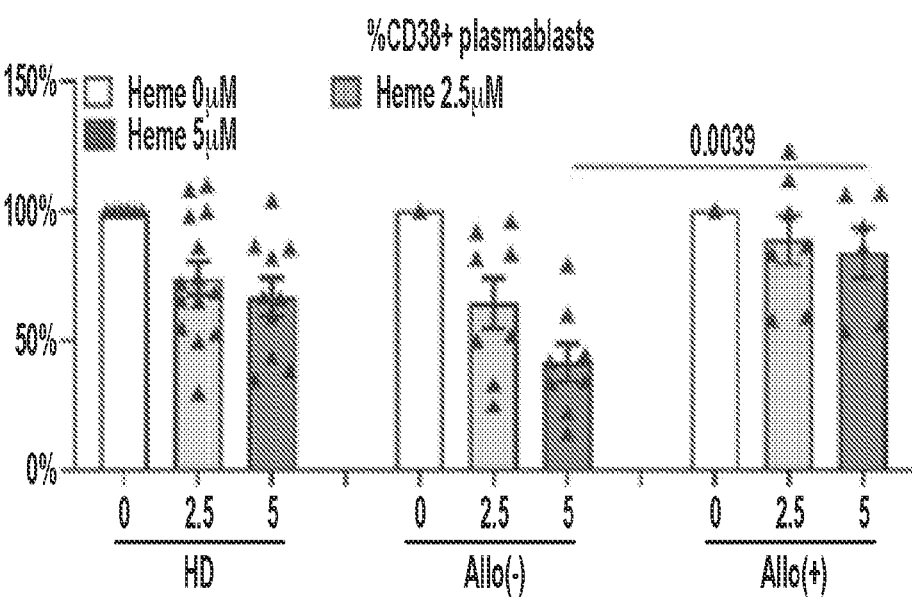

The inhibitory effect of heme on B cell activation may modulate the risk of alloimmunization in hemolytic disorders such as SCD. We compared levels of intravascular hemolysis, specifically total plasma heme levels, between alloimmunized (Allo(+)) and non-alloimmunized (Allo(−)) patients with SCD receiving transfusions, but did not find any significant differences either before or after transfusion (FIG. 1E), suggesting that intravascular heme levels do not correlate with alloimmunized or non-alloimmunized state of a SCD patient. Similarly, no differences were found in any hemolytic indicator such as HbS %, reticulocyte percent, LDH, hemopexin, haptoglobin or bilirubin levels (Table 1), and differentiation of HD naïve B cells into plasmablasts was comparable in the presence of sera from Allo(−) or Allo(+) SCD patients (FIG. 6E). We next tested whether B cell responses to cell-free heme differed in these 2 groups of patients. In the absence of heme, naïve B cells from Allo(−) and Allo(+) SCD patients differentiated comparably into plasmablasts (FIG. 1F). However, B cells from Allo(−) patients were more sensitive to the effects of heme than Allo(+) SCD patients (FIG. 1G) with 58.6%±7.3% inhibition of plasmablast B cell differentiation in Allo(−) SCD patients but only 16%±9.7% in Allo(+) SCD patients at the highest heme (5 µM) concentration (Allo(−) vs Allo(+), p=0.0039). Consistent with the minor effect of heme on healthy donor (HD) B proliferative responses (FIG. 1B), the effect of heme on B cell proliferation did not differ between Allo(−) and Allo(+) patients (FIG. 6F). These data indicate that Allo(−), but not Allo(+), SCD B cells are sensitive to the effects of heme, and that their differentiation into plasma cells is inhibited by hemolysis, raising the possibility that this inhibitory effect of heme may lower the risk of RBC alloimmunization, but only in the Allo(−) SCD group.

TABLE 1

|  | Allo(−) (n = 12) (Average ± S.D.) | Allo(+) (n = 12) (Average ± S.D.) | P value |
|---|---|---|---|
| History of Splenectomy | 9 of 12 | 7 of 12 |  |
| WBC (×10³/µl) | 11.0 ± 3.8 | 12.6 ± 2.2 | 0.22615 |
| Neutrophil (×10³/µl) | 7.4 ± 2.8 | 8.0 ± 1.5 | 0.50134 |
| Lymphocyte (×10³/µl) | 2.2 ± 0.8 | 2.5 ± 0.6 | 0.23106 |
| Monocyte (×10³/µl) | 0.8 ± 0.3 | 0.9 ± 0.1 | 0.11902 |
| Platelet (×10³/µl) | 409.8 ± 70.5 | 425.3 ± 97.3 | 0.72271 |
| Hgb (g/dl) | 9.1 ± 1 | 8.6 ± 0.9 | 0.35888 |
| retic count % | 11.9 ± 4.6 | 12.4 ± 3.1 | 0.73628 |

TABLE 1-continued

| | Allo(−) (n = 12) (Average ± S.D.) | Allo(+) (n = 12) (Average ± S.D.) | P value |
|---|---|---|---|
| retic#/μl | 361.7 ± 103.5 | 420.7 ± 103.7 | 0.21648 |
| HgbS % | 38.2 ± 11.4 | 37.5 ± 7.6 | 0.86117 |
| transfusion (unit) | 518.7 ± 218.3 | 791 ± 438.2 | 0.19469 |
| Hemopexin (ug/ml) | 329.7 ± 276 | 569 ± 499.9 | 0.2195 |
| Haptoglobin (μg/ml) | 48.5 ± 52.4 | 57.8 ± 48.6 | 0.68313 |
| Total heme (μM) | 100.7 ± 49.7 | 113.7 ± 39.9 | 0.50689 |
| LDH (U/L) | 537.6 ± 192.9 | 492.3 ± 111.6 | 0.70605 |
| Total Bilirubin | 7.7 ± 5.4 | 3.6 ± 2.0 | 0.12087 |
| direct Bilirubin | 1.7 ± 2.4 | 0.5 ± 0.3 | 0.21284 |
| ALT | 35 ± 25.7 | 42.9 ± 50.4 | 0.71074 |
| AST | 56 ± 23.8 | 50.3 ± 47.3 | 0.77286 |
| T.I.: recurrent VOC | 33% | 50% | 0.3411 |
| T.I.: stroke prevention | 58% | 58% | 0.6933 |
| T.I.: Spleen Sequestration | 25% | 33% | 0.8077 |

Hemolysis associated indicators in SCD patients (n = 24) receiving chronic RBC exchange, comparing Allo(−) (n = 12) and Allo(+) (n = 12) groups.
VOC: vaso-occlusive crisis;
T.I. = transfusion indication Cell-Free Heme Inhibits Plasma Cell Differentiation Through the DOCK8 Signaling Pathway.

Figures 2A, 2B:
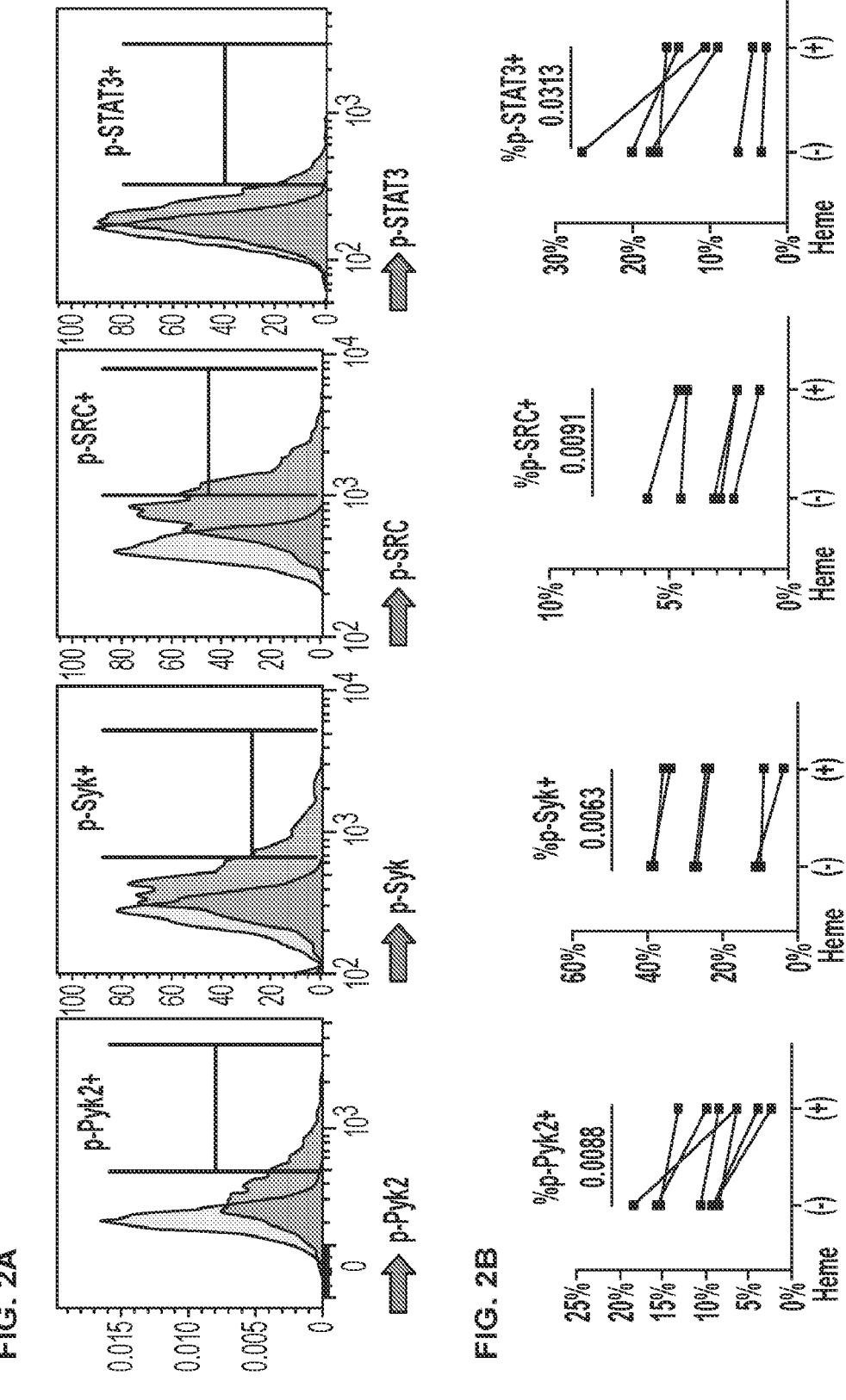
FIG. 2A-G. Inhibition of B cell activation by heme is through DOCK8/STAT3 signaling pathway.
Figure 7A:
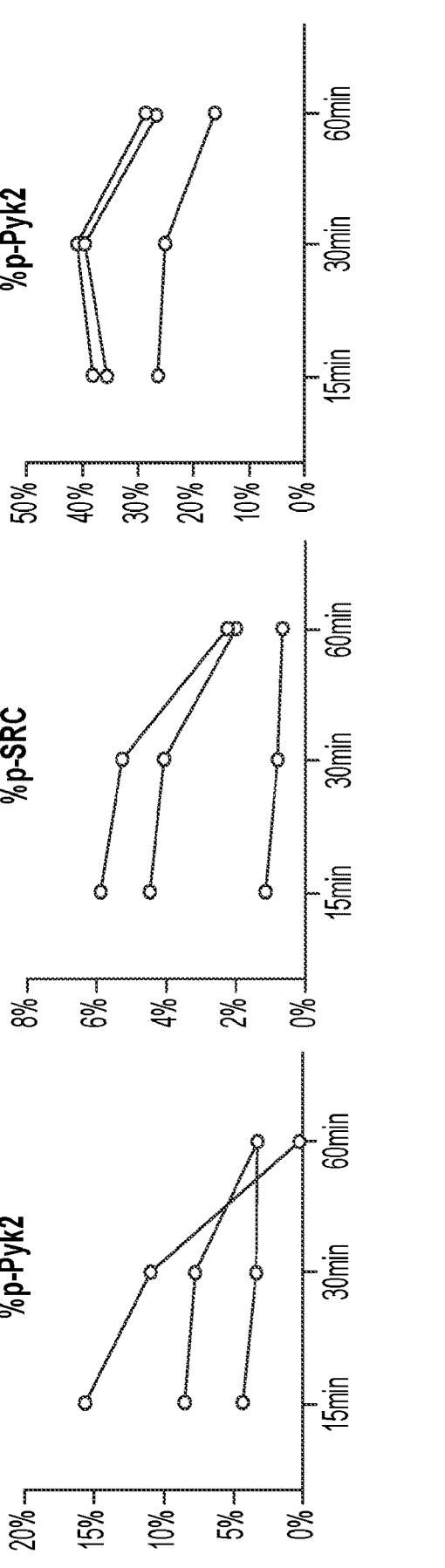
FIG. 7A-C. Effect of heme on B cell STAT3 phosphorylation pathway.
Figure 7B:
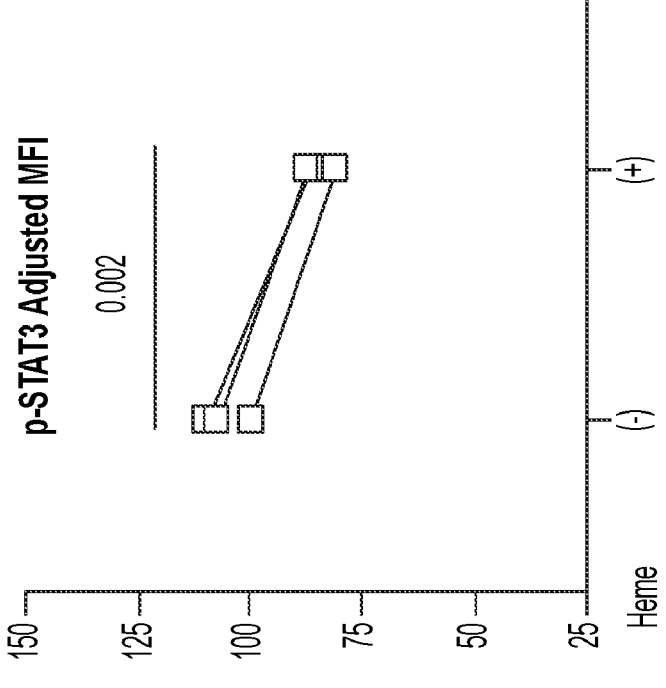
Figure 7B:
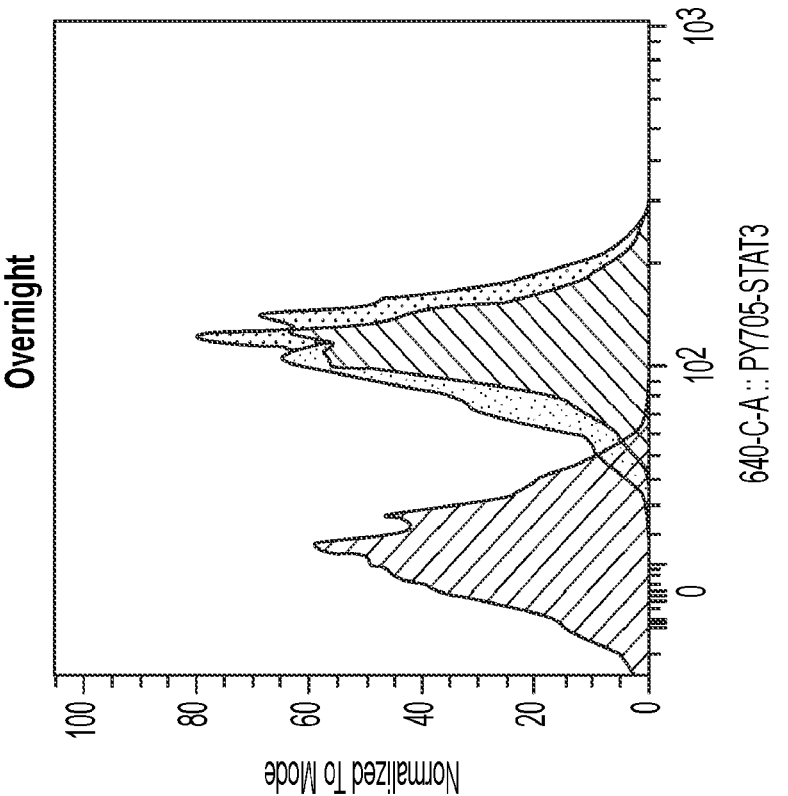
Figure 7C:
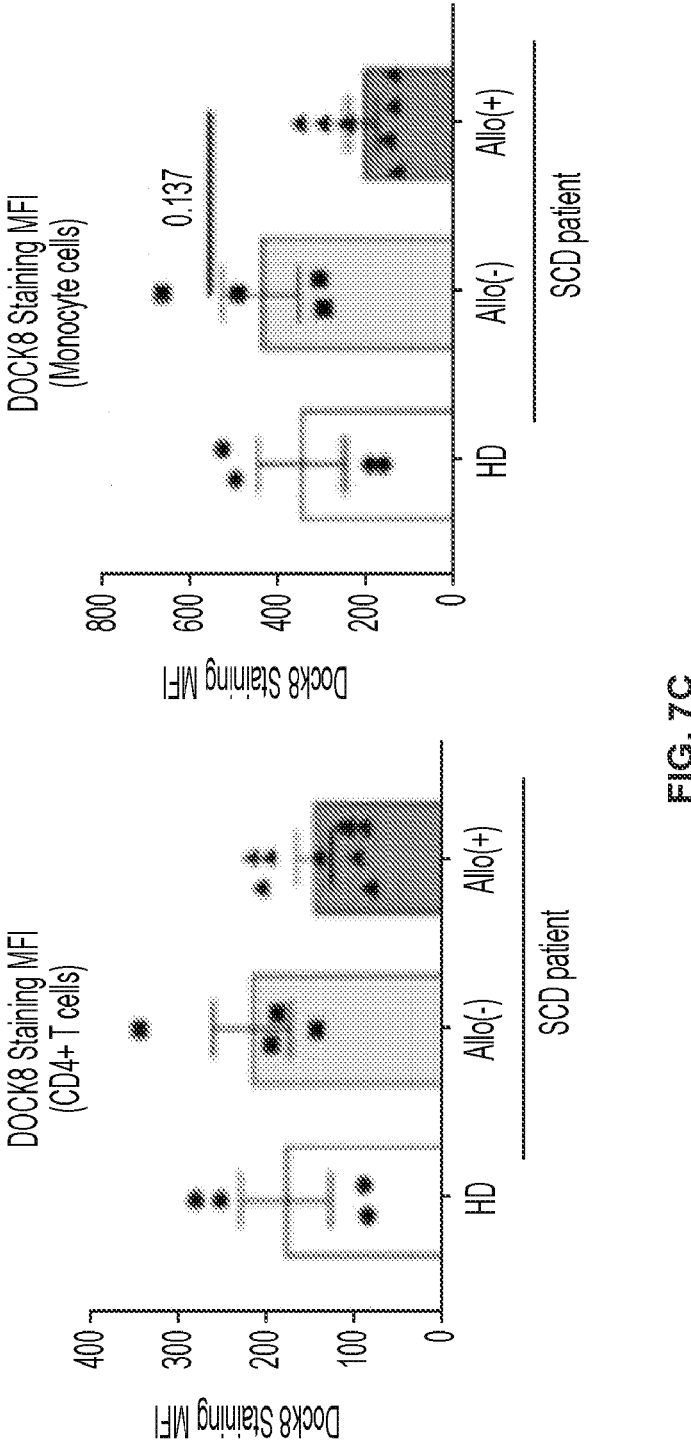

It has been shown that plasma free-heme can directly bind to DOCK8 protein and inhibit monocyte/macrophage phagocytosis through the DOCK8-Cdc42 signaling pathway. DOCK8/STAT3 signaling pathway activation, leading to phosphorylation of Pky2, SYK, SRC, and STAT3, has also been reported to be critical for B cell activation, although the effect of heme on this activation pathway was not examined. To test whether DOCK8/STAT3 signaling is inhibited by cell-free heme during B cell activation, we analyzed the phosphorylation of Pyk2, SYK, SRC, and STAT3 following short-term stimulation in the presence or absence of heme (10 μM) by intracellular flow cytometric analysis. In the absence of heme, stimulation of HD B cells induced phosphorylation of Pyk2, SYK, SRC, and STAT3, (FIG. 2A). Heme treatment resulted in significant reduction in the levels of phosphorylated (p)-Pyk2/SYK/SRC/STAT3 (FIG. 2B) (p=0.0088, 00063, 0.0091, 0.0313, respectively). The inhibitory effect of heme on p-STAT3 was confirmed in overnight samples (FIG. 7B) Levels of p-Pyk2/SRC/SYK were decreased by 60 min and were not analyzed after that time point (FIG. 7A). These data indicate heme-mediated reduction of several key phosphoproteins in the DOCK8/STAT3 signaling pathway in B cells, consistent with inhibition of B cell DOCK8/STAT3 activation by heme.

Figure 2C:
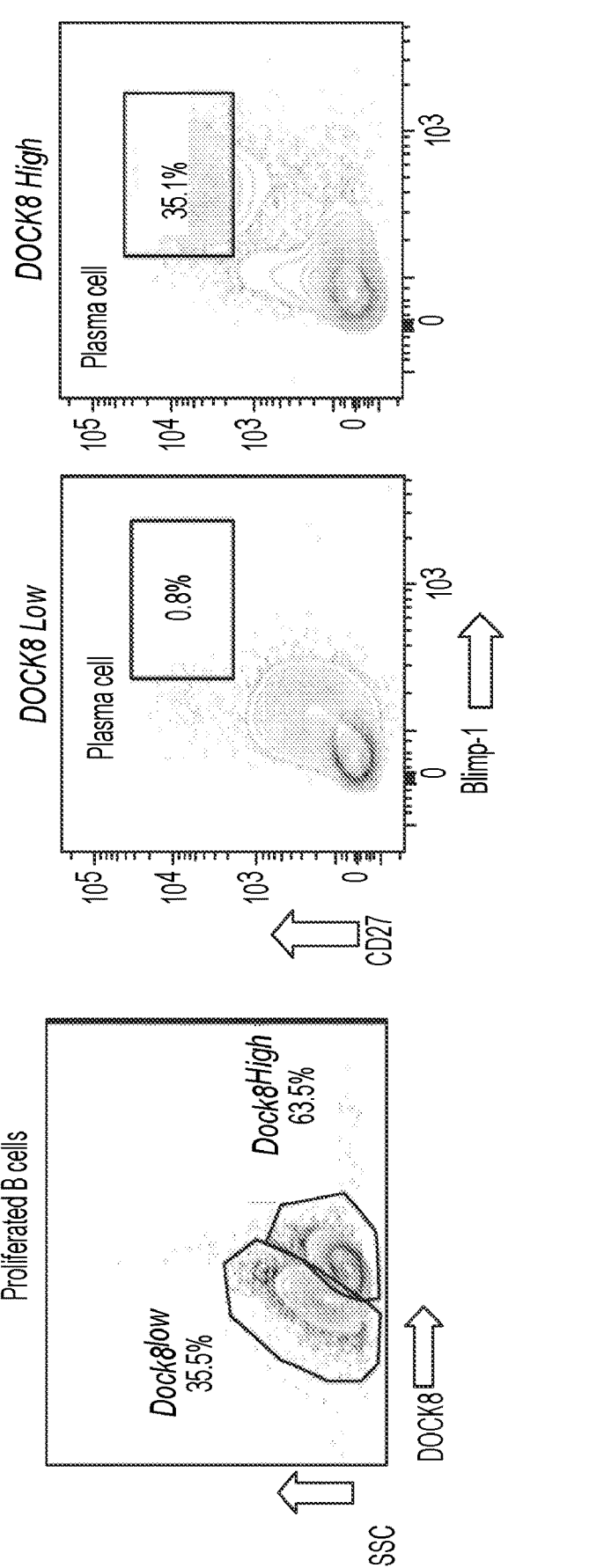
Figure 2D:
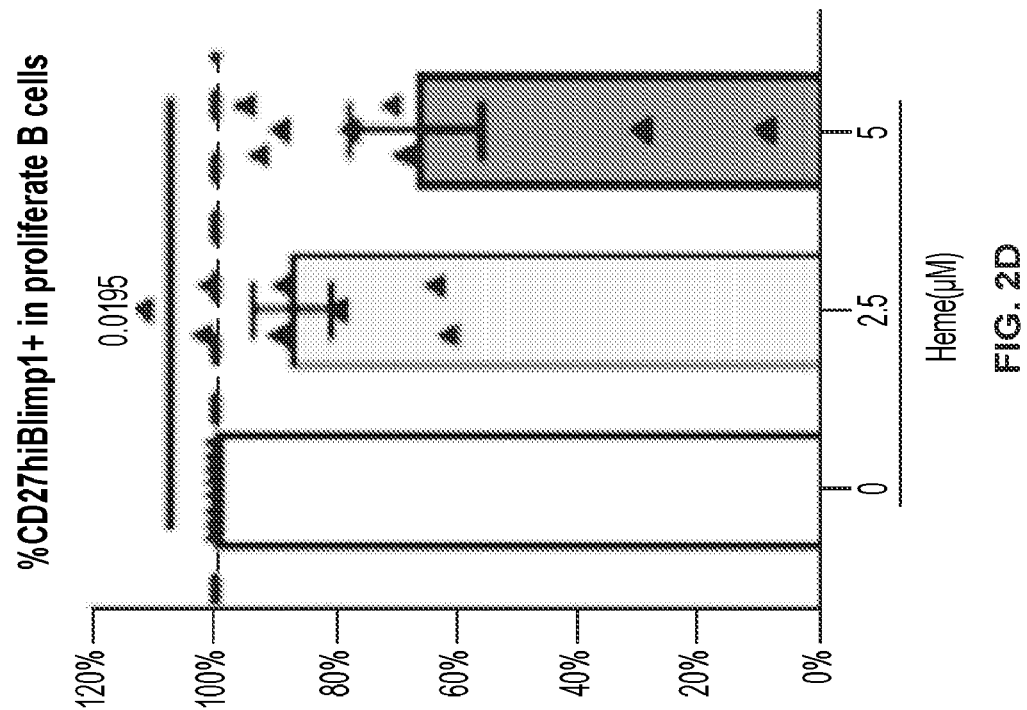
Figure 2E:
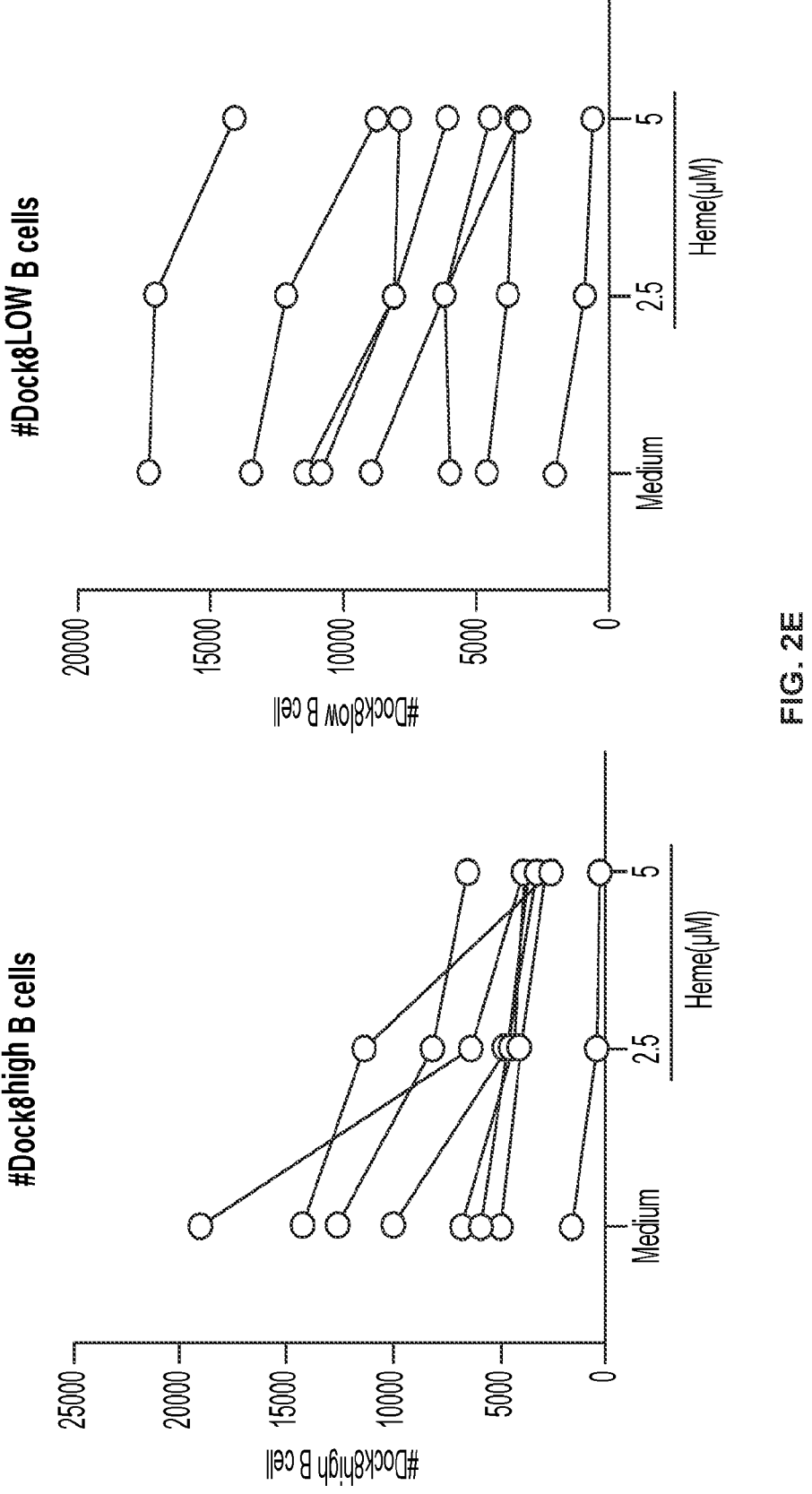
Figure 2E:
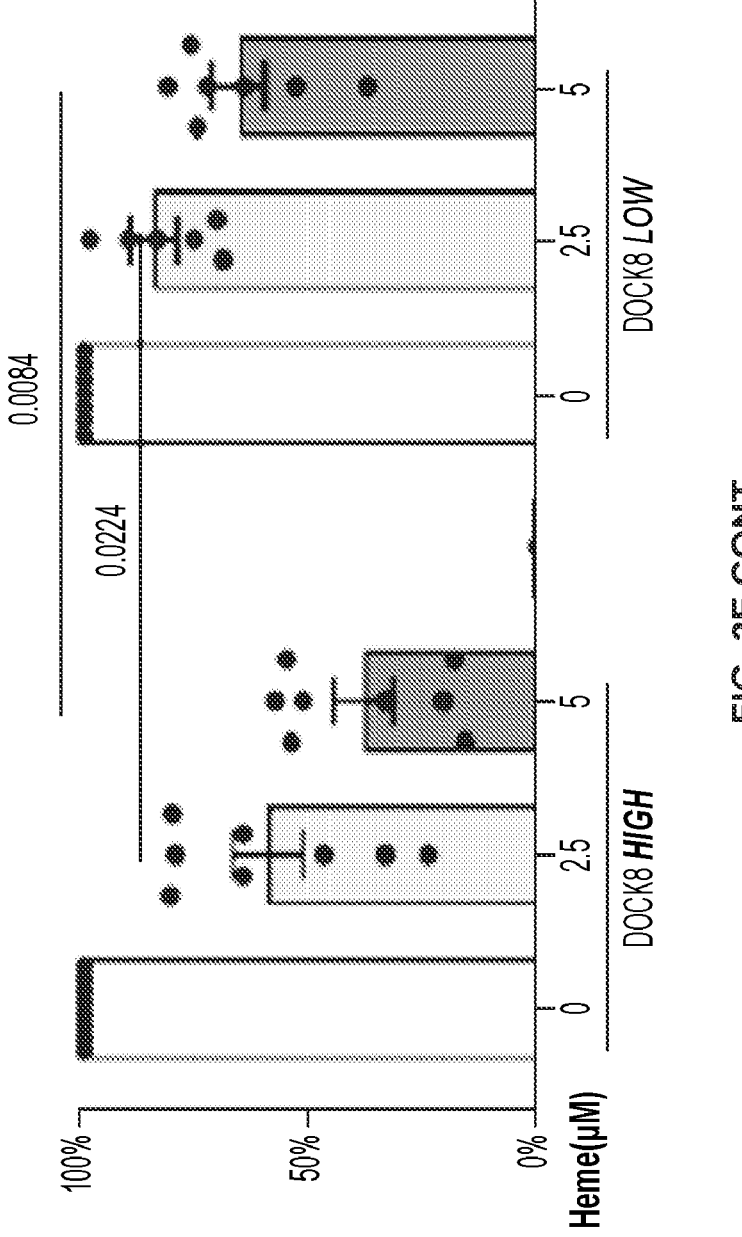
Figure 2F:
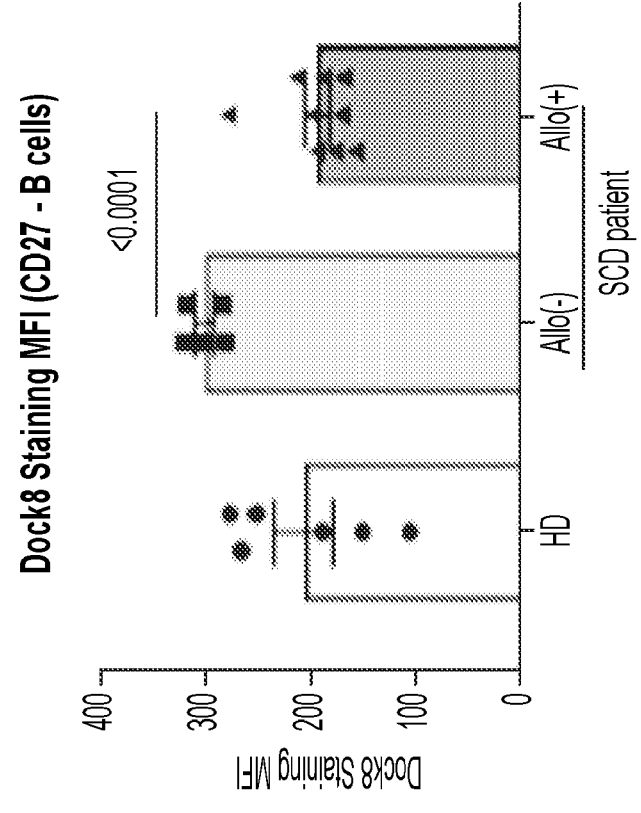
Figure 2F:
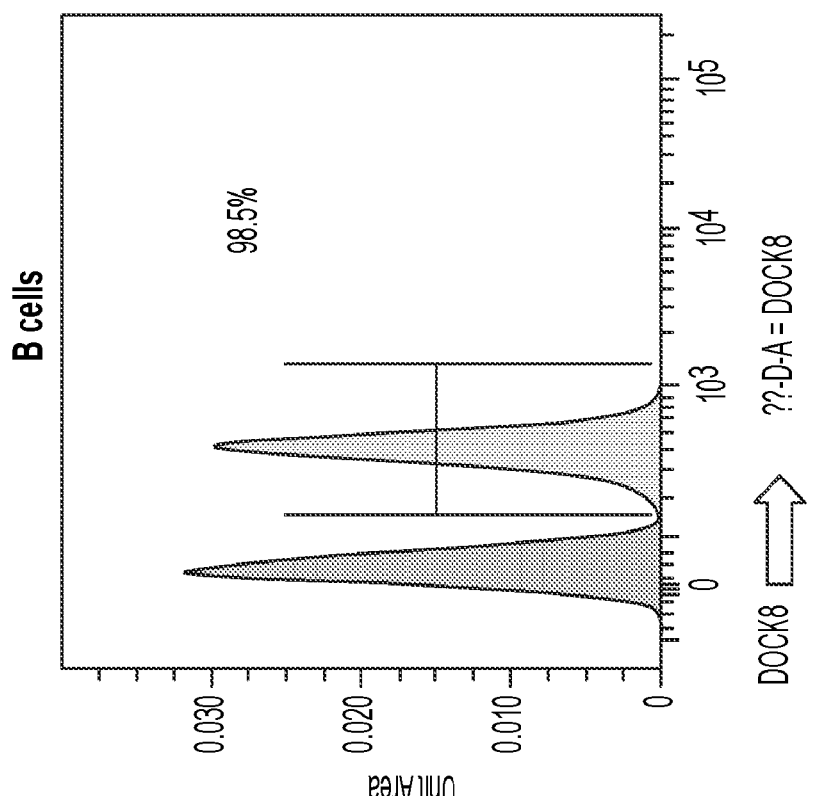
Figure 2G:
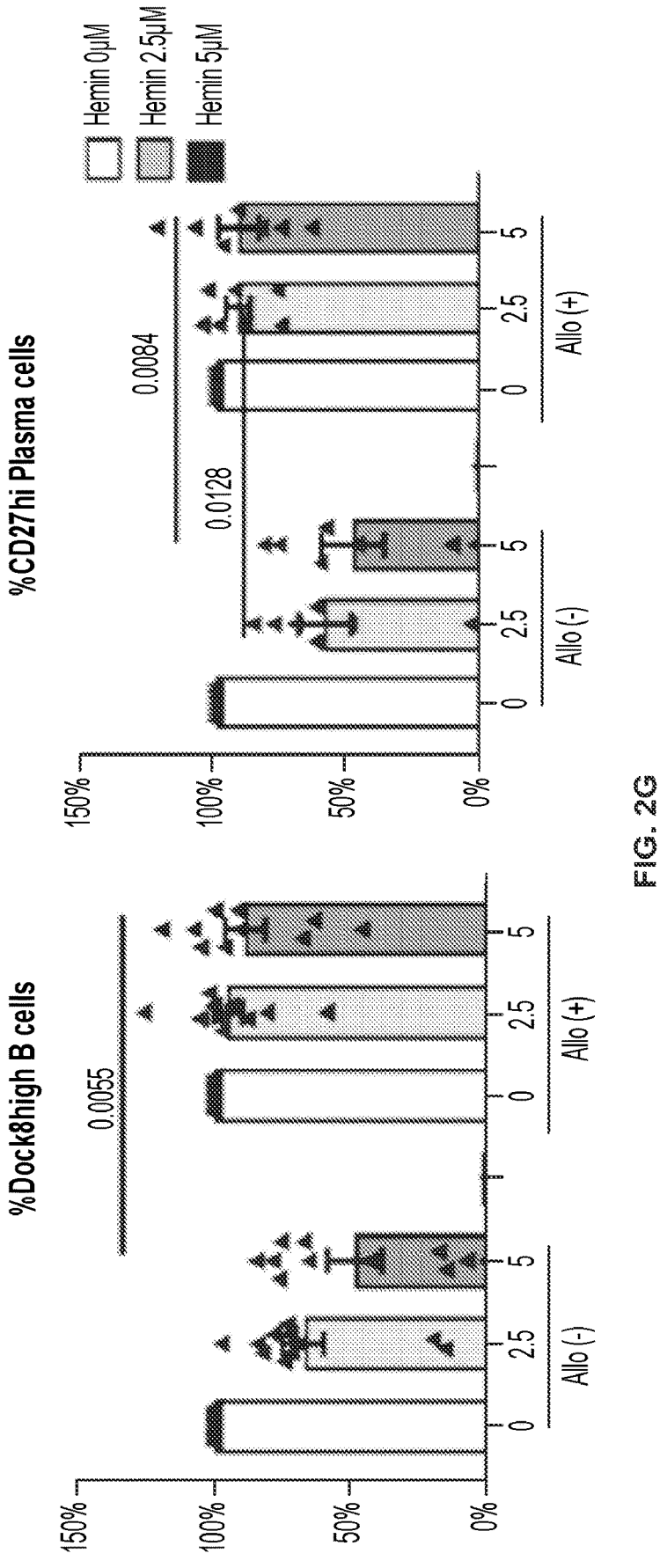

We next tested the effect of cell-free heme on DOCK8 signaling during B cell differentiation. Strikingly, we found that stimulated B cells could be divided into DOCK8 high (DOCK8$^{hi}$) and DOCK8 low (DOCK8$^{lo}$) cell subsets based on DOCK8 expression (FIG. 2C, left). Using CD27 and Blimp-1 as plasma cell markers, we found that CD27$^{hi}$Blimp-1$^{+}$ plasma cells were mostly within the DOCK8$^{hi}$ rather than the DOCK8$^{lo}$ subset (FIG. 2C, right). Heme treatment led to inhibition of CD27$^{hi}$Blimp-1$^{+}$ plasma cell differentiation (FIG. 2D, p=0.0195). We also found a dose-dependent decrease of DOCK8 expressing cells in stimulated B cells, with a more robust reduction in DOCK8$^{hi}$ than DOCK8$^{lo}$ subsets (61.6%±6.5% vs 34.1%±5.9% at 5 μM: p=0.0084, FIG. 2E), suggesting that DOCK8$^{hi}$ cells are preferentially inhibited by heme and that heme inhibits plasma cell differentiation by targeting DOCK8$^{hi}$ activated B cells.

Figure 3A:
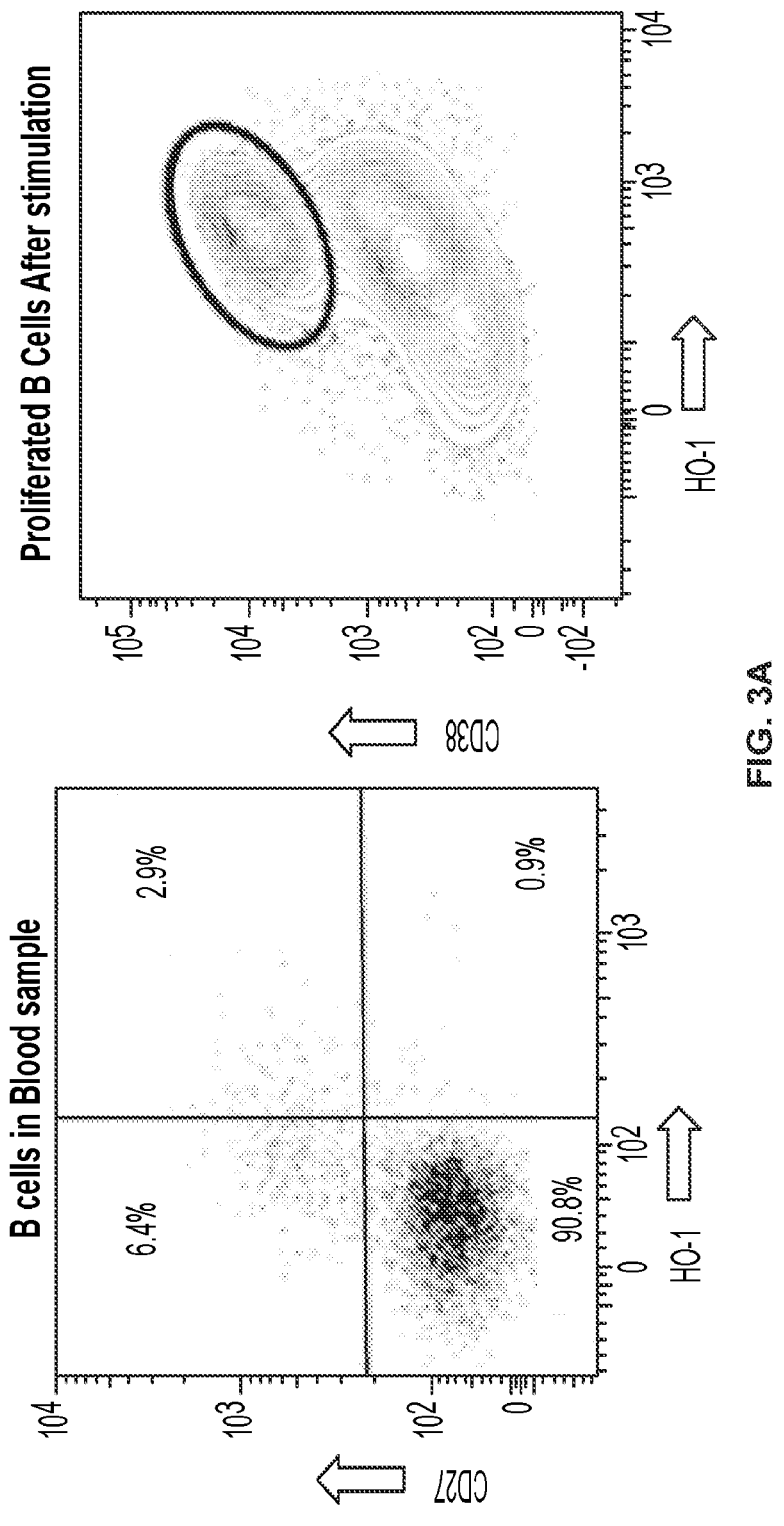
FIG. 3A-F. Role of HO-1 enzyme activity in heme-mediated B cell activation.
Figure 3C:
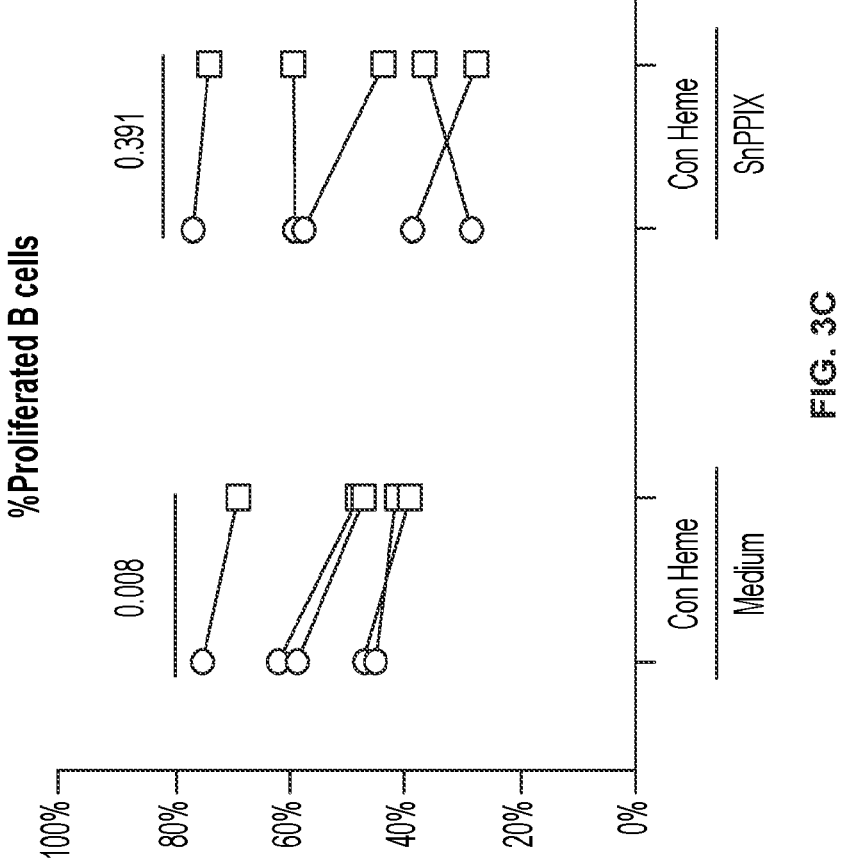
Figure 3B:
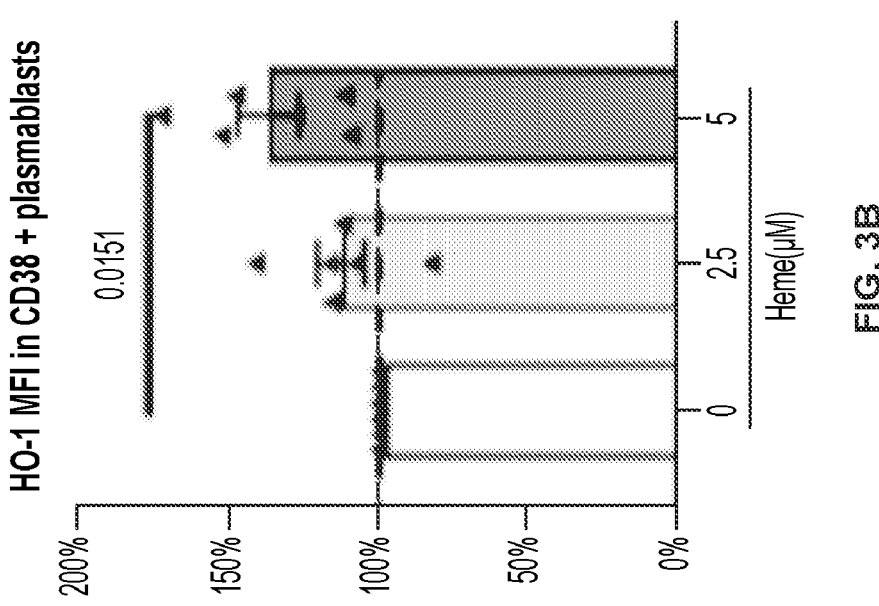
Figure 3D:
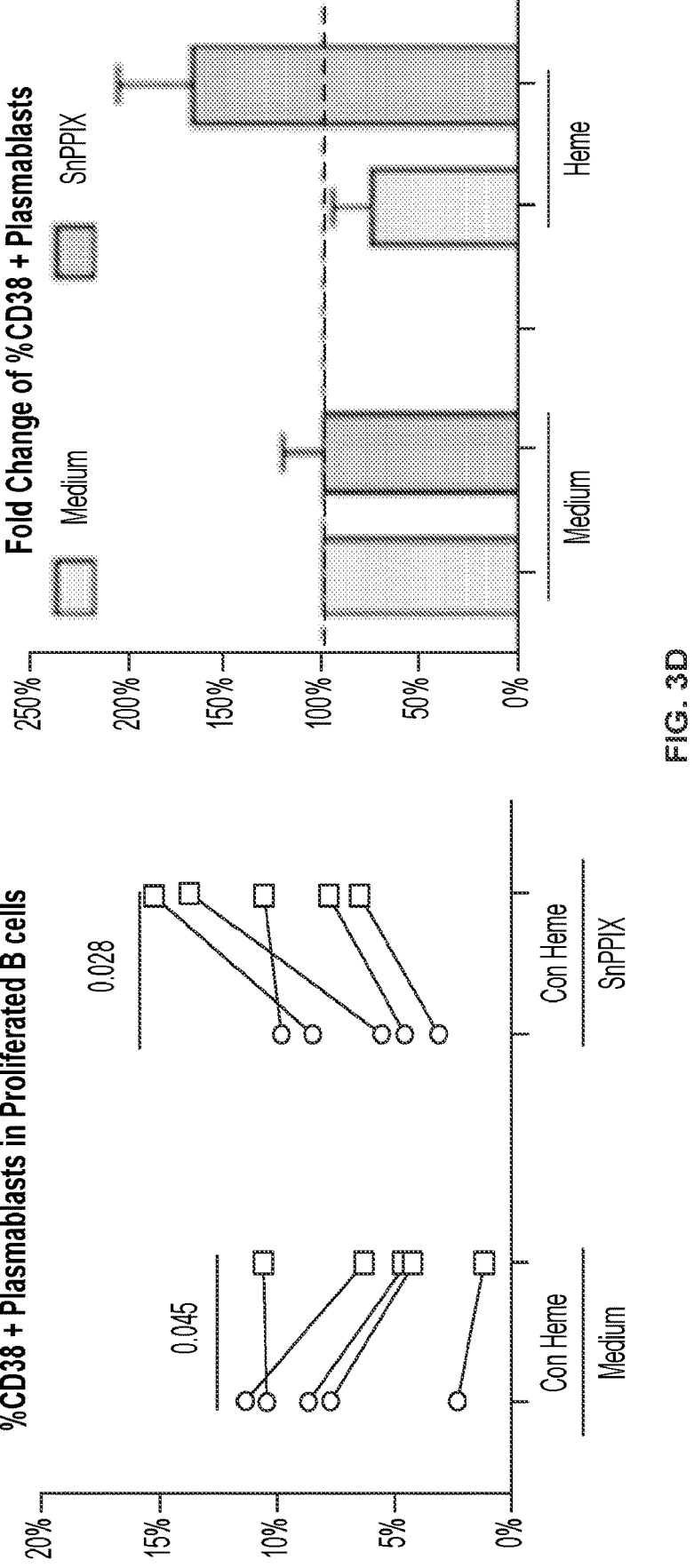
Figure 3E:
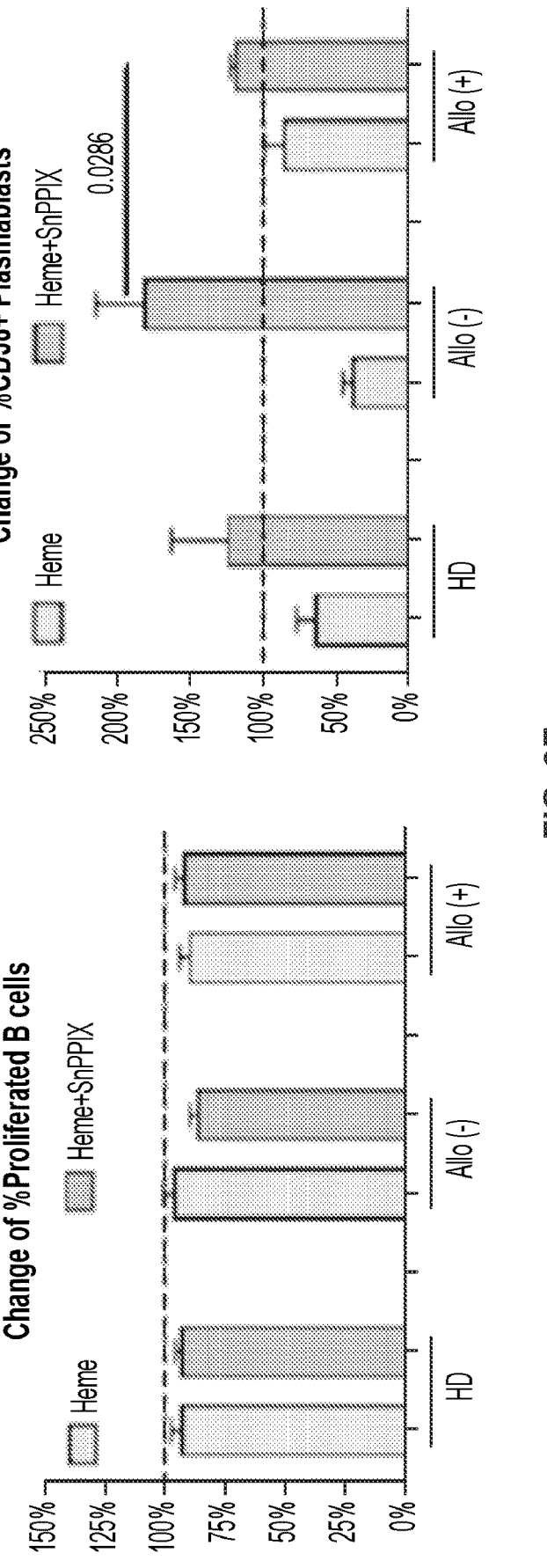
Figure 3F:
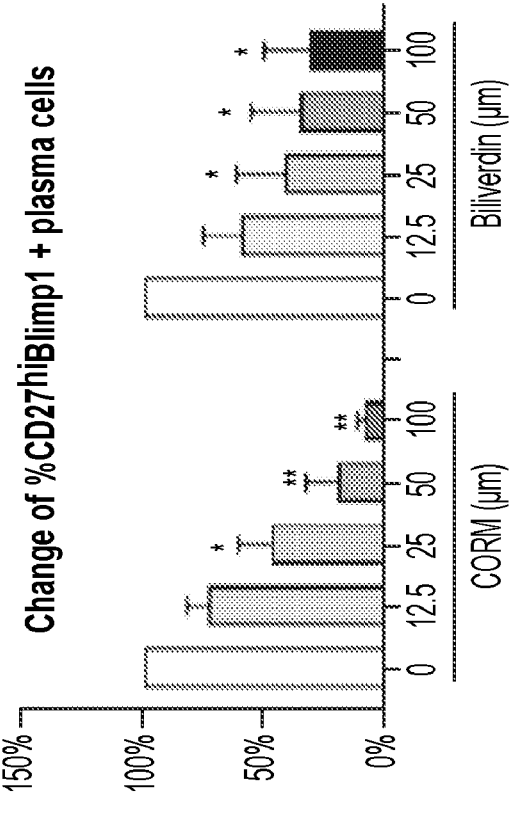
Figure 3F:
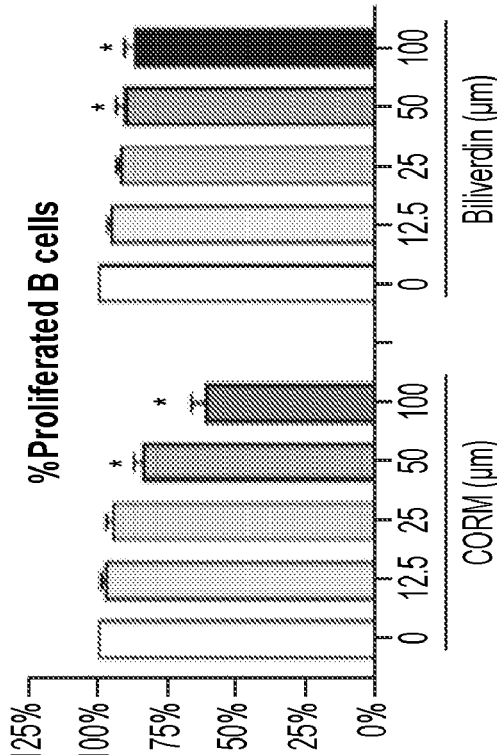

To test whether DOCK8 expression is associated with differential heme responses, we measured intracellular DOCK8 expression in circulating B cells, and as controls, in T cells and monocytes. Almost all B cells were DOCK8 positive, but DOCK8 levels were significantly higher in Allo(−) as compared to Allo(+) B cells (FIG. 3F, p<0.0001). Importantly, heme inhibited DOCK8$^{hi}$ B cells and CD27$^{hi}$Blimp-1$^{+}$ plasma cell differentiation in Allo(−) SCD patients but not in Allo(+) patients, suggesting that DOCK8 expression levels may be associated with heme response in B cells and SCD alloimmunization risk.

Home Inhibits B Cell Activation Through Modulation of HO-1 Enzyme Activity.

Figure 8A:
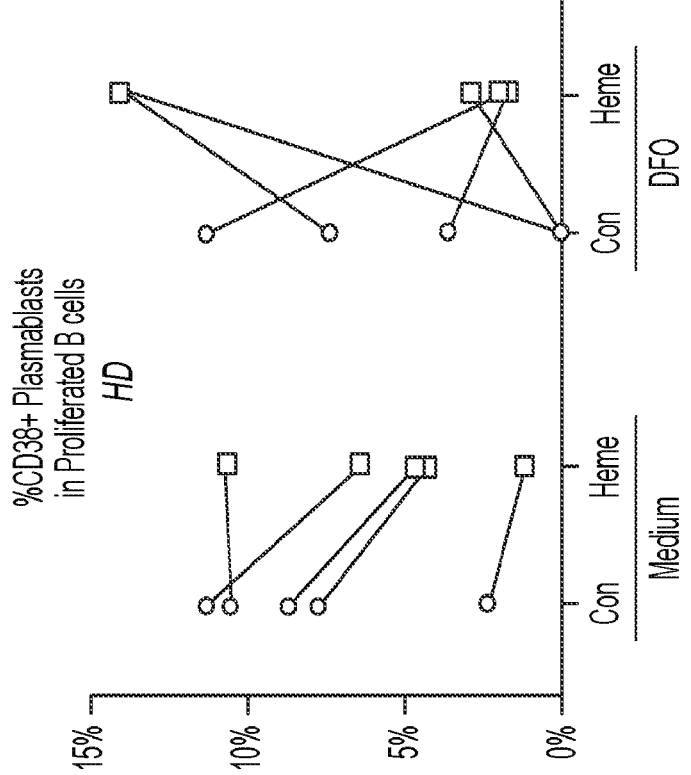
FIG. 8A-B. Effect of iron chelation in the presence of heme on plasmablast differentiation.
Figure 8B:
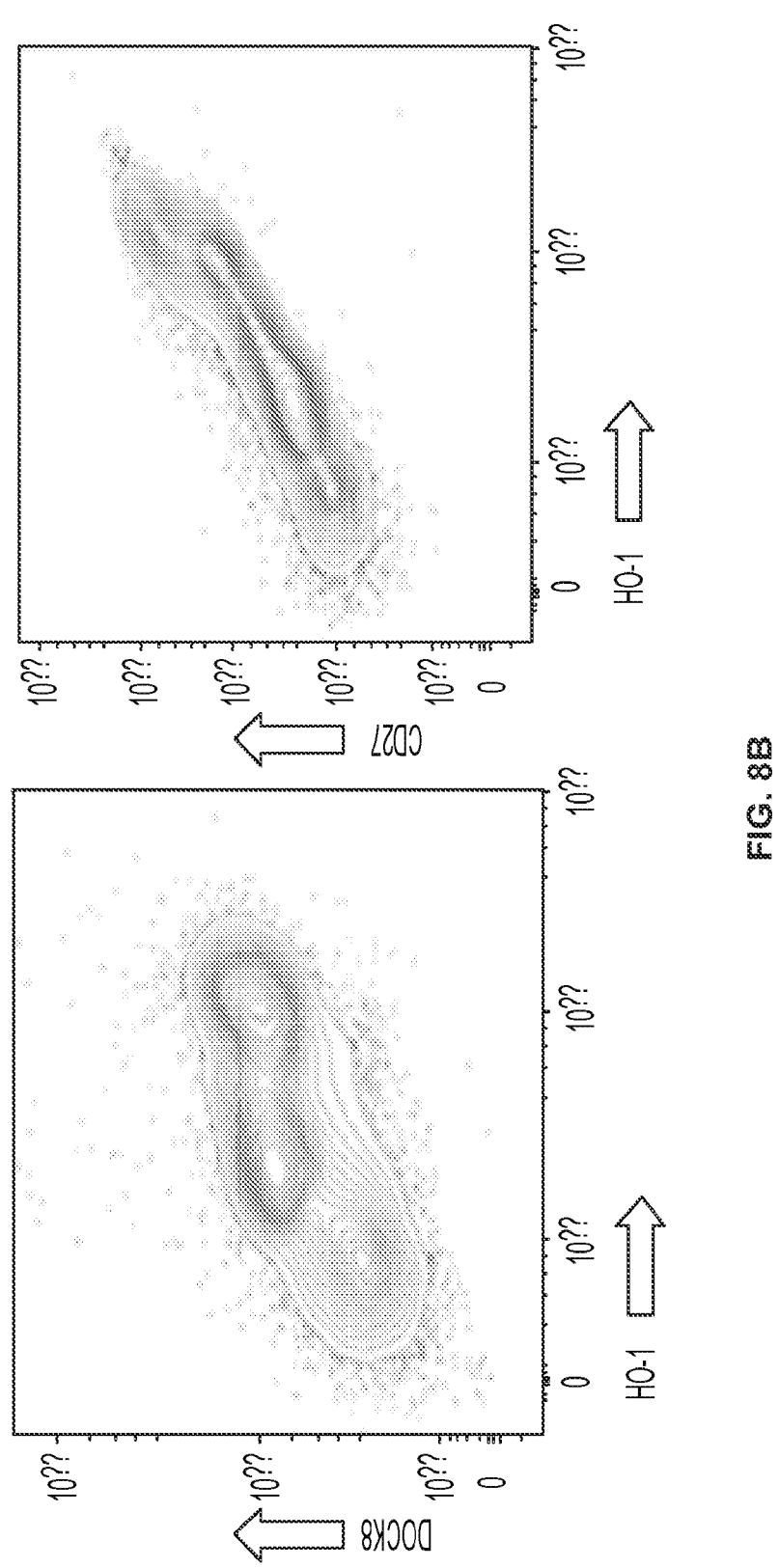

The inhibitory effect of heme on B cell activation may involve other signaling pathways than just DOCK8/STAT3. HO-1 is a key enzyme for heme degradation with multiple biologic activities attributed to its enzymatic byproducts. We analyzed HO-1 expression levels in human B cells before and after stimulation with our polyclonal B cell activation cocktail. HO-1 expression was low in B cells before stimulation (FIG. 3A, left-side), but increased significantly following stimulation, mostly in CD38+ plasmablasts (FIG. 3A, right-side) and was further induced by treatment with heme (FIG. 3B). We also found higher HO-1 levels in DOCK8$^{hi}$ plasma cells (FIG. 8B).

To examine the role of HO-1 enzymatic activity in heme-mediated inhibition of B cell activation, B cells were stimulated in the presence of heme without or with SnPPIX (2.5 μM), a competitive HO-1 inhibitor which blocks its activity. Pretreatment with heme or SnPPIX alone or heme+SnPPIX had little to no effect on B cell proliferation (FIG. 3C), indicating that HO-1 was largely devoid of pro- or anti-proliferative activity. In contrast, heme-mediated inhibition of plasmablast cell differentiation was reversed by SnPPIX, and heme+SnPPIX treatment led to an even higher frequency of plasmablasts compared to no treatment (FIG. 3D), suggesting that inability to degrade heme may induce plasma cell differentiation by other, as yet unknown, pathways. SnPPIX alone had no effect on differentiation (8.1%±3.5% vs 6.3%±2.7%, p>0.3, FIG. 3D), indicating that basal intracellular heme levels are too low to provide enough substrate for HO-1 enzymatic activity to inhibit B cell differentiation. We also tested the effect of SnPPIX on SCD Allo(+) and Allo(−) B cell activation. B cell proliferative responses were comparable in the presence of SnPPIX in the 2 groups (FIG. 3E). In contrast, SnPPIX reversed heme-mediated inhibition of plasmablast differentiation in Allo(−) SCD patients, but had less effect in Allo(+) SCD patients (FIG. 3E), suggesting a more profound inhibitory effect of HO-1 in B cells from Allo(−) SCD patients. Altogether, these data suggest that HO-1 enzymatic activity is involved in abetting decreased plasmablast B cell differentiation by heme and that HO-1-mediated inhibition of activated B cells is more pronounced in Allo(−) than Allo(+) SCD patients.

HO-1 can degrade heme into carbon monoxide (CO), iron and biliverdin. Iron chelation at high concentrations inhibited both B cell proliferation and differentiation while in low concentrations had inconsistent effects (FIG. 8). In contrast, treatment with carbon monoxide releasing molecule-3 (CORM-3) and exogeneous biliverdin inhibited B cell proliferation and plasma cell differentiation in a dose-dependent manner with more robust effects on plasma cell differentiation than B cell proliferation (FIG. 3F, CO: 91.2%±2.9% VS 38.7%±5.0%; biliverdin: 68.4%±18.6% VS 13.3%±3.5% at the highest concentrations). These data are consistent with a role for the HO-1 enzymatic byproducts CO and biliverdin in the inhibition of plasma B cell differentiation.

Quinine Enhances the Heme Inhibitory Effect on B Cell Activation in Both Allo(−) and Allo(+) SCD Patients.

Figure 4A:
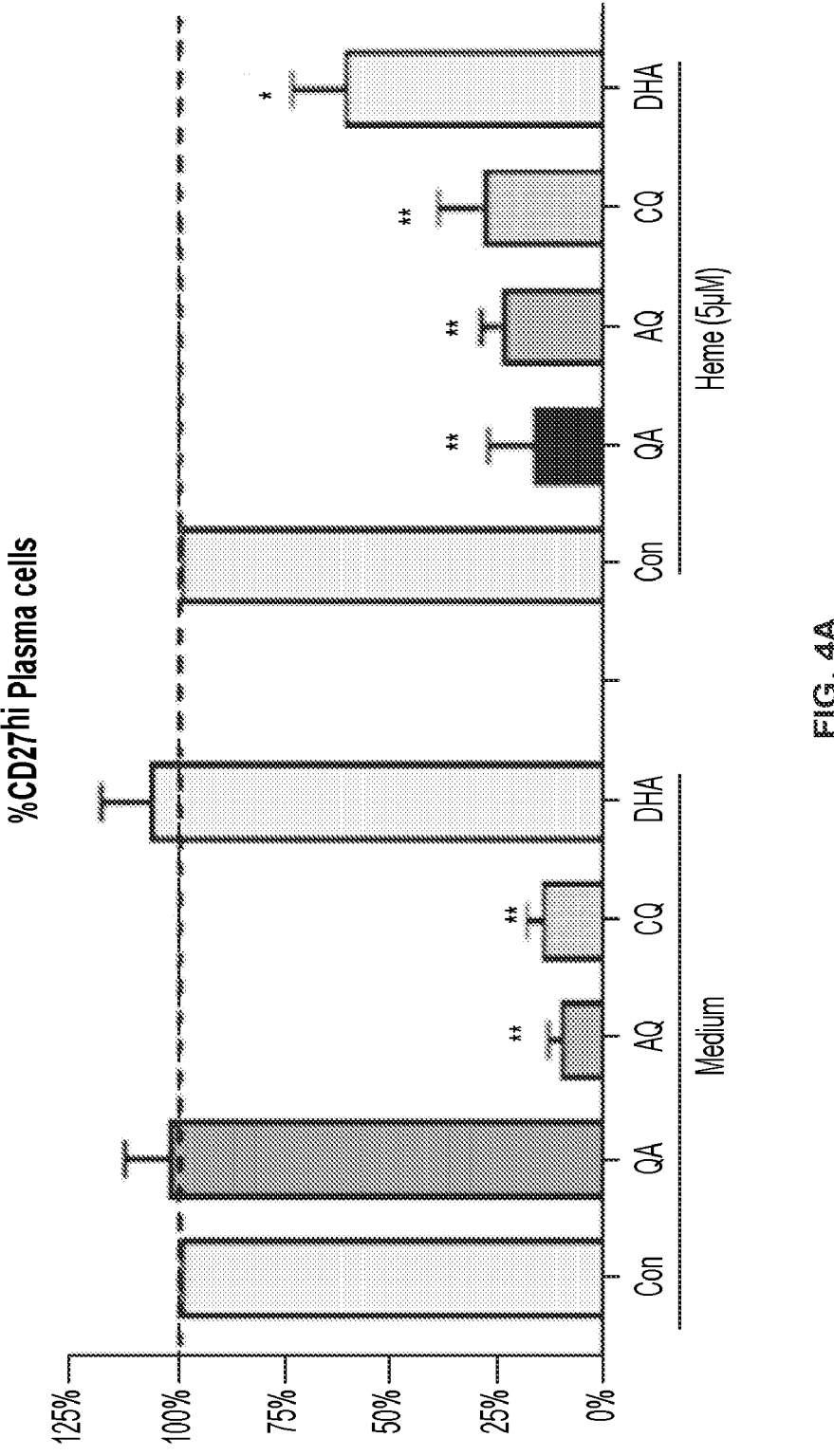
FIG. 4A-E: Quinine increases heme-mediated inhibition of B cell activation. Fold change in plasma cell frequency in 7-day stimulated purified naïve HD B cells in the presence of (FIG. 4A) 2.5 μM quinine (QA), amodiaquine (AQ), chloroquine CQ, and dihydroartemisinin (DHA0 without or with 5 μM heme relative to untreated but stimulated cultures, or (FIG. 4B) different doses of quinine plus 2.5 μM or 5 μM heme.
Figure 4B:
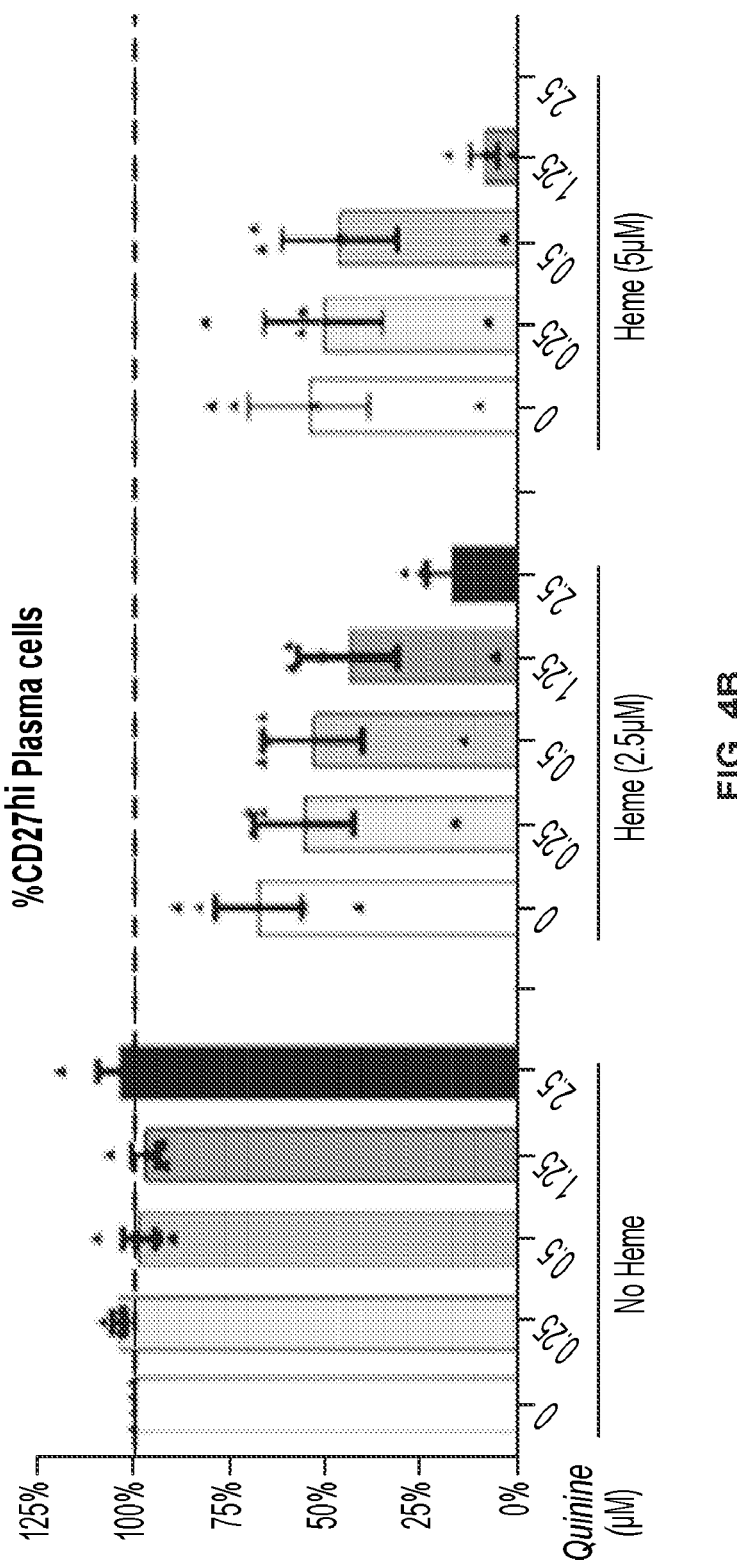
Figure 9A:
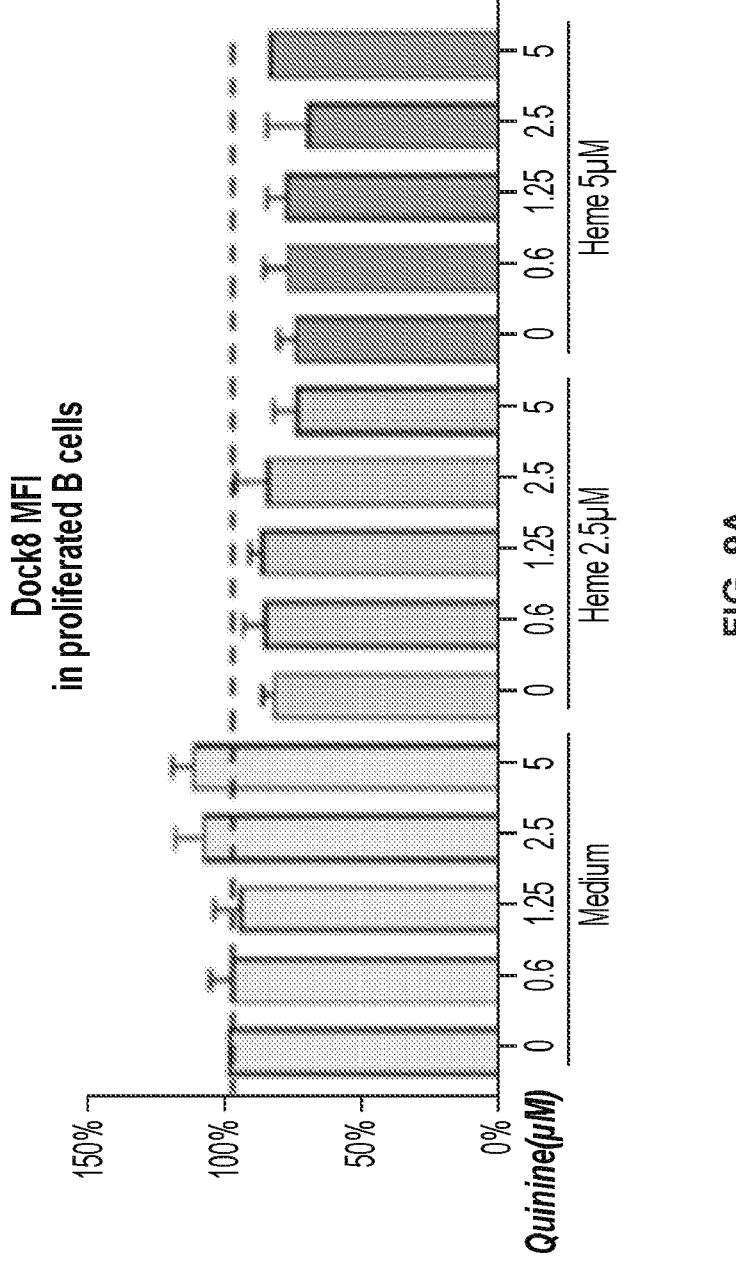
FIG. 9A-B. Effect of quinine on B cell DOCK8 expression.
Figure 9B:
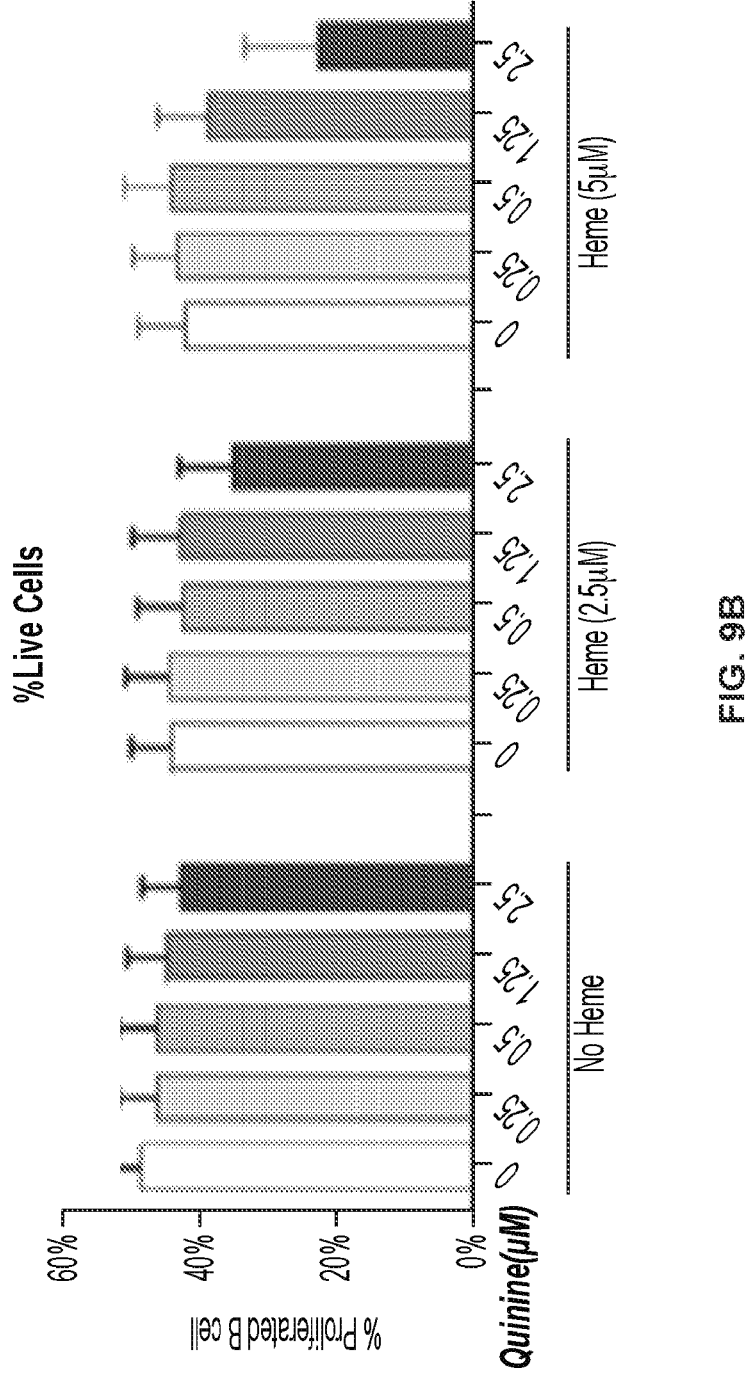

Several small molecule-based anti-malarial drugs have been developed based on their ability to bind and alter heme bioactivity. Some of these molecules may also alter the B cell inhibitory properties of heme, and may, in some cases, further bolster heme's inhibitory effects and even reverse refractoriness to heme-mediated B cell inhibition as seen in SCD Allo(+) patients. To test this, several heme binding molecules including quinine (QA), chloroquine (CQ), amodiaquine (AQ), and dihydroartemisinin (DHA) were tested on HD B cell responses. AQ and CQ inhibited plasma cell differentiation in the absence or presence of heme, whereas the inhibitory effect of quinine and DHA on B cells required the presence of heme with a more robust inhibition by quinine than DHA (FIG. 4A). Quinine inhibition was dose-dependent, and at higher doses of heme and quinine (2.5 µM), we found an almost complete inhibition of plasma cell differentiation (FIG. 4B), consistent with an additive effect on suppression of B cell activation. Of note, although all analysis was restricted to live cells, viability studies indicated minimal cytotoxic effects of quinine except at the highest doses of heme plus quinine (FIG. 9B).

Figures 4C, 4D:
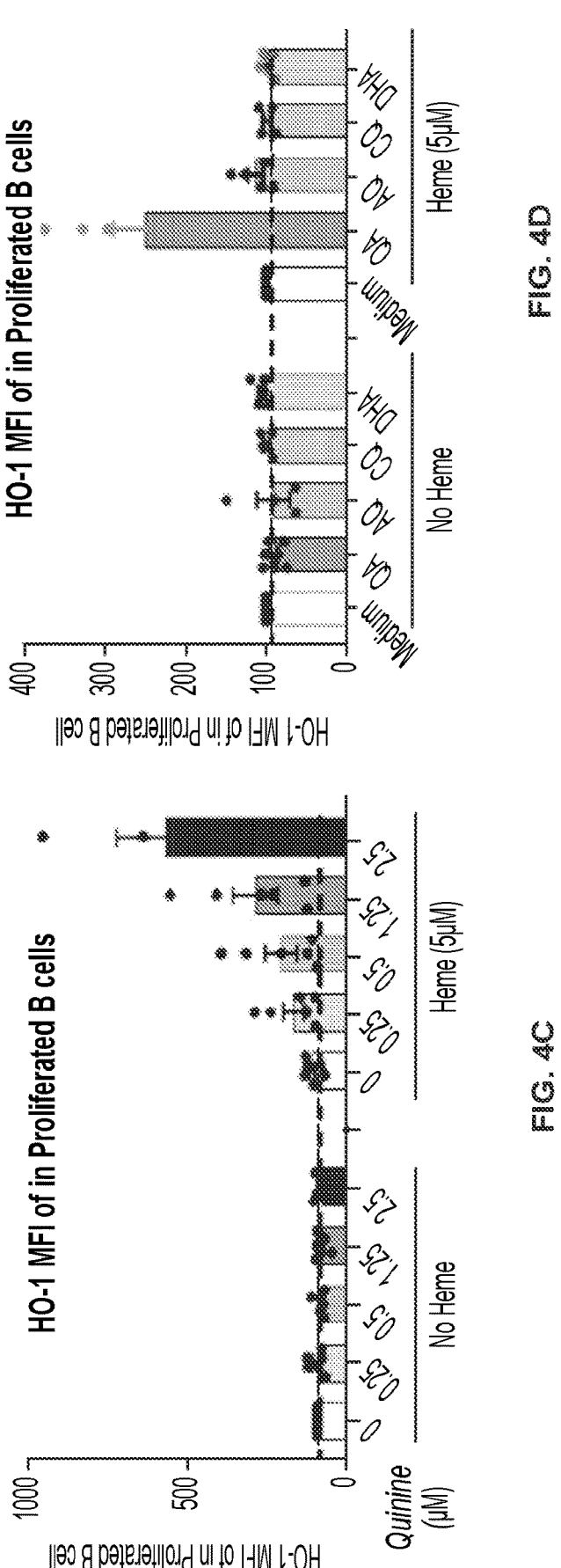

We next tested the effect of quinine on DOCK8 and HO-1 expression in stimulated B cells in the presence of heme. Quinine had no significant effect on DOCK8 expression (FIG. 9A), but we found a dose-dependent increase in HO-1 expression in proliferated B cells in the presence of heme and quinine (5-fold increase at the highest dose, FIG. 4C). HO-1 upregulation only occurred in heme plus quinine stimulated B cells, but not with the other heme binding molecules AQ, CQ or DHA (FIG. 4D). Given that HO-1 inhibits B cell activation (FIG. 3), these data suggest that inhibition of plasma cell differentiation by heme and quinine is likely through induction of HO-1 expression.

Figure 4E:
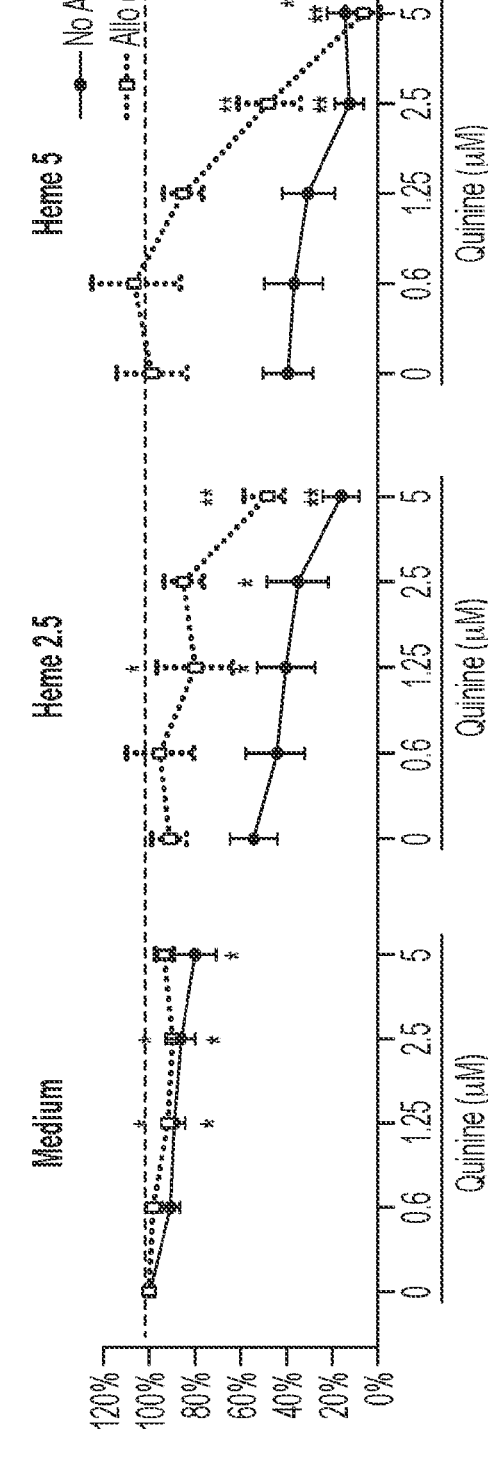

Finally, we examined the effect of quinine on B cells from Allo(−) and Allo(+) SCD patients. Quinine had a weak but significant inhibitory effect on plasma cell differentiation in the absence of heme in both groups of SCD patients (FIG. 4E), possibly due to residual heme within SCD B cells. In Allo(−) SCD patients, quinine further increased heme-mediated suppression of plasma cells (FIG. 4E), but more importantly, it reversed resistance to heme suppression in Allo(+) patients, resulting in inhibition of plasma cell differentiation of heme-treated B cells (FIG. 4E), thus underscoring its therapeutic potential for decreasing SCD alloimmunization.

Discussion:

In the present study, we demonstrated that hemolysis regulates human B cell activation, inhibiting plasmablast/plasma cell differentiation. Mechanistically, heme targeted DOCK8$^{hi}$ plasma cells, inhibiting the STAT3 signaling pathway in stimulated B cells. The inhibitory effects of heme on activated B cells were also mediated through HO-1 enzymatic activity and specifically the HO-1 byproducts CO and biliverdin. Compared to non-alloimmunized SCD patients, B cells from alloimmunized SCD patients expressed lower levels of DOCK8 and were less responsive to inhibition by heme and HO-1. These data support our working model in which B cell intrinsic signals sensing heme/hemolysis control the humoral immune response to allogenic transfusions, and ultimately RBC alloimmunization in SCD patients. This study has thus unraveled a novel mechanism of humoral immunity suppression by hemolysis, with potential for identifying new therapeutic targets as well as B cell-associated biomarkers of alloimmunization in SCD (FIG. 5).

Several genome-wide association studies have identified genetic variants as potential risk factors for alloimmunization in SCD. Most are likely to target steps in the humoral immune response, starting with activation of innate immune antigen presenting cells through to CD4+ helper T cells and ultimately B cells. Our previous studies have identified abnormal responses in several of these immune subsets in Allo(+) SCD patients, including CD16+ monocytes, dendritic cells, the immunosuppressive regulatory T cells (Tregs) and T follicular helper cells. Along with the present study, these data support a proposed model of a heightened humoral immune response in Allo(+) patients leading to a higher risk of RBC alloimmunization. It is likely that increased alloimmunization risk in Allo(+) SCD patients is due to cumulative impaired heme responses in more than one immune effector cell type, including lower HO-1 expression in CD16$^+$ monocytes leading to inefficient Treg expansion in hemolytic conditions, insensitivity to heme-mediated inhibition of dendritic cell maturation and altered B cell activation in response to heme. No differences were found in hemolysis-associated indices between alloimmunized and non-alloimmunized SCD patients, including total plasma heme, bilirubin or LDH levels or reticulocyte percentages, suggesting that not hemolysis level per se, but rather the immune cell-intrinsic response to hemolysis, is a determinant of alloimmunization risk. RBC destruction and production, resulting in elevated heme release, mainly occurs in the spleen and/or bone marrow. Thus, B cell heme response is likely to play a more important role in RBC alloimmunization, which occurs primarily in the spleen than in other humoral responses such as vaccine responses, which mostly develop in the lymph nodes or at sites of vaccine delivery (muscle/skin). The differential impact of heme on B cell development in the various lymphoid organs likely accounts for why no differences are detected in the overall circulating B cell subset numbers and frequencies between alloimmunized and non-alloimmunized SCD patients. Differentiation of memory B cells into plasma cells was not affected by heme.

Figure 10A:
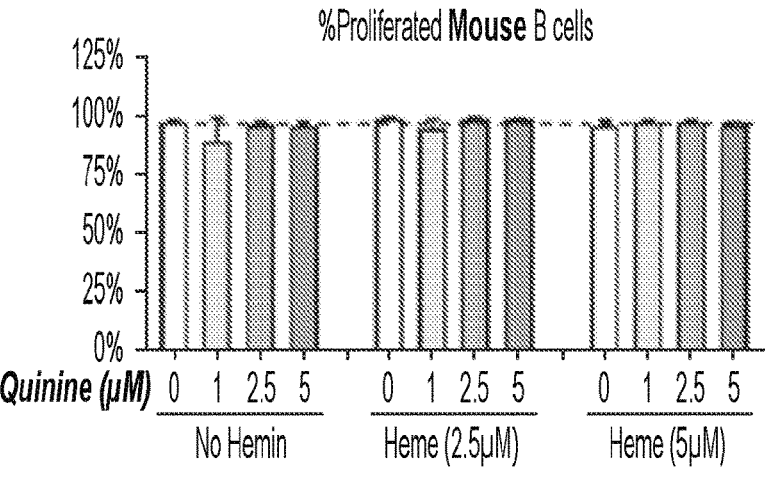
FIG. 10A-C. Effects of heme and quinine on mouse B cell differentiation in vitro: Splenic B cells were purified from C57BL/6J mice (n=3), stained with CFSE and cultured (5×10⁴/well) for 7 days in the presence of anti-mouse IgM, IgG F(ab)'₂ (10 μg/ml), anti-mouse CD40 antibody (1 μg/ml)
Figure 10B:
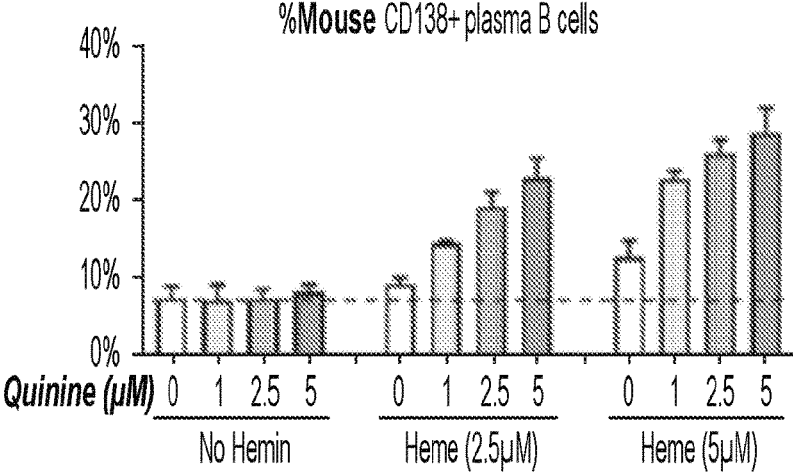
Figure 10C:
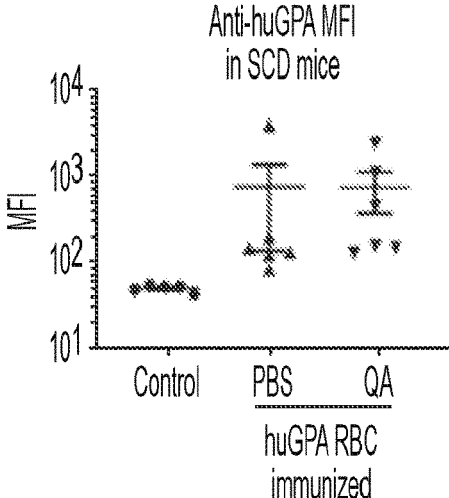

Our finding that heme inhibits human plasma B cell differentiation in vitro differs from mouse data showing increased plasma B cell differentiation through Bach2. We found very low levels of Bach2 in human B cells before and after stimulation, with no significant change even in the presence of heme, suggesting that Bach2 response to heme differs between human and mouse B cells. In the published studies, LPS was used to stimulate mouse B cells. However, TLR4, the receptor that responds to either LPS or heme, is not expressed on human B cells. Thus, instead of LPS, we used a cocktail of anti-IgG/IgM, anti-CD40 and CpG to activate human B cells. Interestingly, similar B cell activation cocktails cause mouse B cells to differentiate into plasma cells in vitro. However, addition of heme or heme plus quinine did not inhibit mouse plasma cell differentiation (FIG. 10B), and treatment of SCD mice with quinine did not lower RBC alloimmunization levels in vivo (FIG. 10C). These data indicate clear differences between human and mouse B cell response to heme, irrespective of the B cell activation stimuli.

We have identified an unexpected relationship between DOCK8 expression levels in activated B cells and response to heme. Functionally-altered DOCK8 models have been highly informative of DOCK8's role in immunity, as have studies of DOCK8 protein expression levels in immune cells or disease states. For example, the reduced Treg DOCK8 levels in patients with atopic dermatitis is likely responsible for reduced Treg-derived IL-10 and TGF-β expression and low DOCK8 expression can cause impaired neutrophil migration in patients with myelodysplastic syndrome (MDS), whereas high DOCK8 expression leads to increased leukemic cell survival in acute myeloid leukemia. Together with our data, these studies suggest that DOCK8 expression can be a potential biomarker as well as therapeutic target in various disorders.

DOCK8 levels did not correlate with hemolysis levels in SCD patients, consistent with our proposed model that it acts as a heme sensor within B cells. In hepatocellular carcinoma cells, CD147 activation induces DOCK8 expression through SRC signaling and STAT3 phosphorylation. Our data indicate that heme inhibits B cell STAT3 phosphorylation, potentially leading to a decrease in DOCK8$^{hi}$ B cell numbers. Another potential B cell regulator of DOCK8 expression is miR-34a, shown to inhibit neutrophil DOCK8 expression in MDS. miR-34a regulates B cell development by inhibiting the transition of pro-B cells into pre-B cells and its expression is inhibited by HO-1 enzymatic activity.

Figure 11:
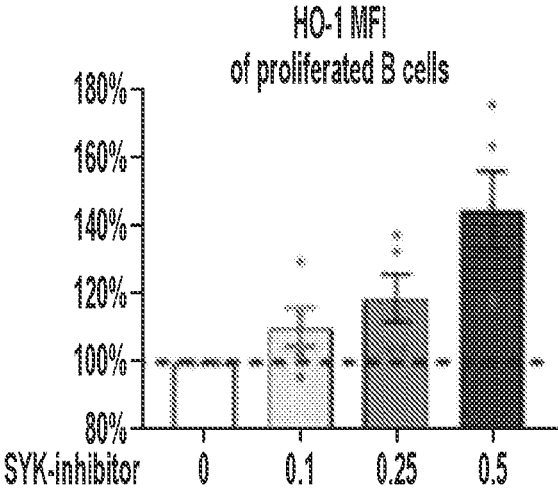
FIG. 11: DOCK8/STAT3 signaling pathway blockade and HO-1 expression: Fold change in in HO-1 expression in proliferated B cells from 7-day stimulated HD naïve B cells treated with SYK inhibitor, Syk Inhibitor II, relative to no SYK inhibitor.

Our study has uncovered two signaling pathways, namely through STAT3 and HO-1, responsible for heme-mediated inhibition of B cells. For example, STAT3 in monocytes/macrophages and endothelial cells was shown to mediate HO-1 induction by IL-10 and IL-6, respectively. STAT3 was also reported to be essential for the protective effects of HO-1 in oxidant-induced lung injury. The effect of HO-1 on STAT3 activity is more complex. HO-1 inhibited STAT3 activation in endothelial and prostate cancer cells. In contrast, in various disease models, HO-1 activated STAT3 by increasing STAT3 phosphorylation. Thus, the interaction between HO-1 and STAT3 likely depends on cell type and disease state. Interestingly, using a selective SYK inhibitor, which is expected to inhibit the DOCK8/STAT3 signaling pathway, we found induction of HO-1 in stimulated B cells (FIG. 11), suggesting that heme may induce HO-1 in B cells through blocking DOCK8 signaling.

Identification of CO and biliverdin, two byproducts of HO-1 enzyme activity, as potent inhibitors of plasma B cell differentiation is a key finding of our study and further supports the role of HO-1 enzymatic activity in suppressing B cell development. CO mediates its anti-proliferative and anti-inflammatory effects through binding hemoproteins such as soluble guanylate cyclase (sGCS) and P38 MAPK. In addition to its antioxidant activity, biliverdin can activate aryl hydrocarbon receptor (AhR) signaling. AhR is expressed at low levels in resting B cells but is highly upregulated following activation. AhR inhibits plasma B cell differentiation by suppressing several key B cell transcription factors including Blimp-1, XBP1, and STAT3 phosphorylation. The B cell response to heme in SCD may be through the biliverdin/AhR pathway and that B cell sensitivity to biliverdin may be an alloimmunization risk factor, opening up the prospect of using biliverdin and/or other AhR agonists as therapeutic candidates for preventing RBC alloimmunization in SCD patients.

An exciting finding of our study is that B cell response to heme can be modulated by heme-binding small molecules. Specifically, in the presence of quinine, B cells from alloimmunized SCD patients were no longer resistant to the inhibitory effects of heme. This raises the potential for therapeutic novel use of quinine for inhibition of alloimmunization in SCD patients. These results also indicate that heme-binding small molecules do not simply neutralize free heme like the heme scavenger hemopexin, but rather exhibit potent immune-modulating activity, possibly through forming a complex with heme. In the case of quinine, the immunomodulatory mechanism is likely mediated through upregulation HO-1 since heme plus quinine induced a 5-fold increase in HO-1 levels in stimulated B cells. In the present of study, we focused on the effects of heme and quinine on B cell differentiation into plasma cells. Heme plays a critical role in sickle cell pathophysiology and given its immunomodulatory role, altered immune activation may further contribute to sickle complications. Identification of heme-binding small molecules with novel immunomodulatory properties offers the potential for their use for prevention and/or reversion of SCD complications as well as other hemolytic conditions.

Figure 12:
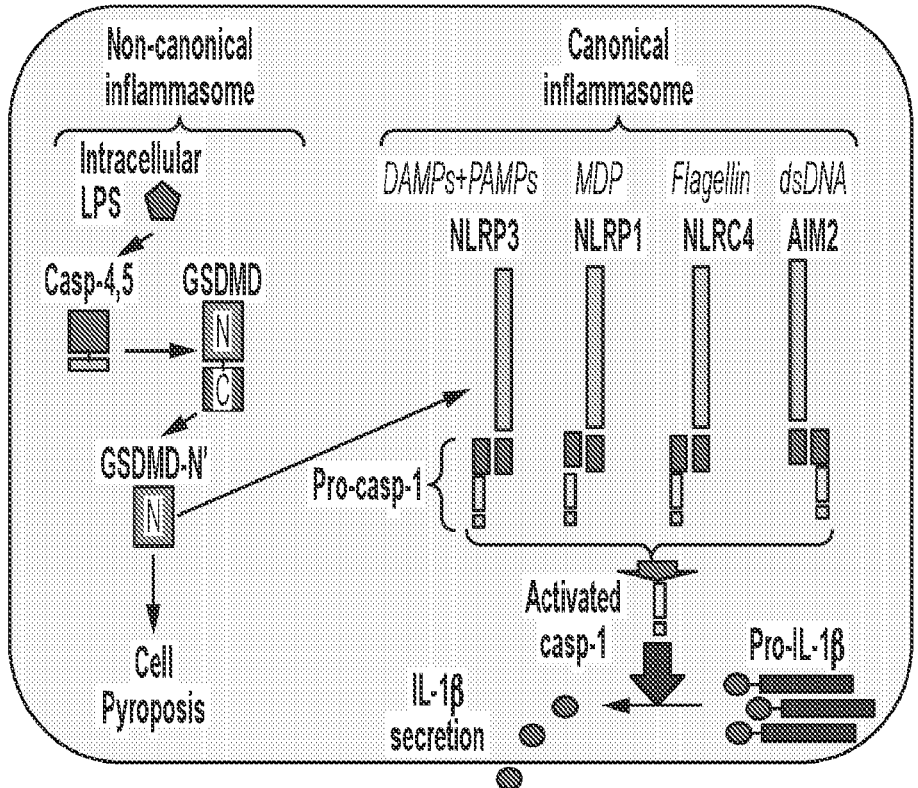
FIG. 12 depicts a diagram of inflammasome signaling pathway.

Example 2. Hemolysis Inhibits Inflammasome Activation in Sickle Cell Disease The inflammasome signaling pathway is a key host inflammatory response that promotes IL-1$\beta$ production by processing pro-IL-1$\beta$ into cleaved mature IL-1$\beta$. It is activated in numerous inflammatory diseases with pharmacological inhibition of inflammasome pathway considered as a promising therapeutic strategy in several inflammatory disease models (Guo H et al. Nat Med. 21:677-87, 2015; Mangan M S J, et al. Nat Rev Drug Discov. 17:588-606, 2018. The inflammasome pathways include both canonical and non-canonical pathways (FIG. 12) with NLRP3 activation pathway considered the most important since it can sense various DAMP and PAMP stimuli.

Figure 13A:
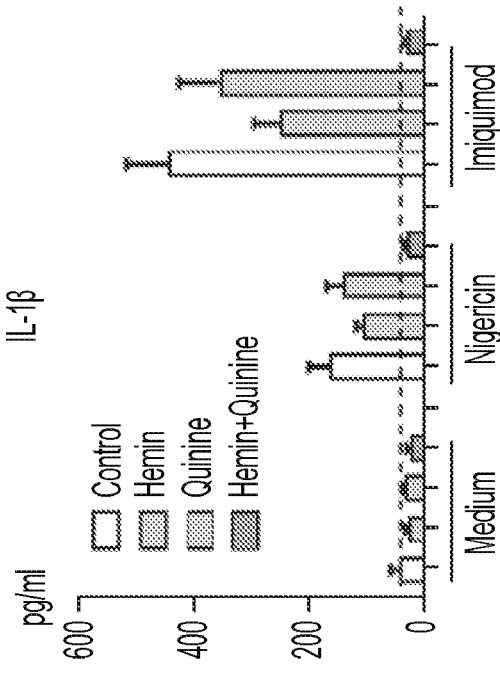
Figure 13A:
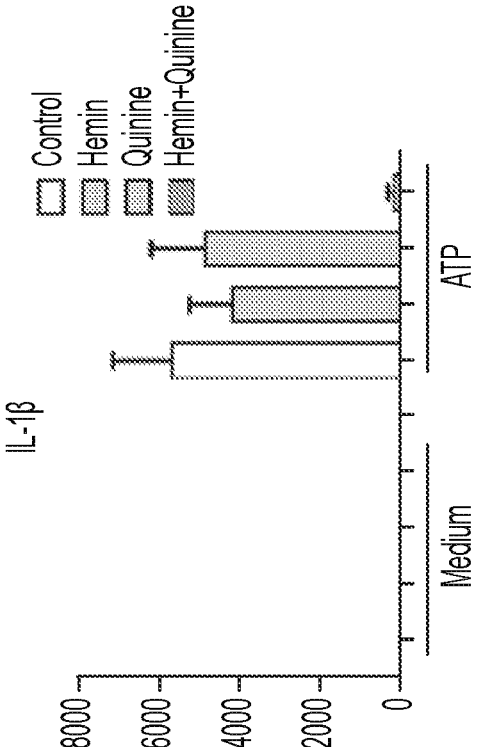
Figure 13C:
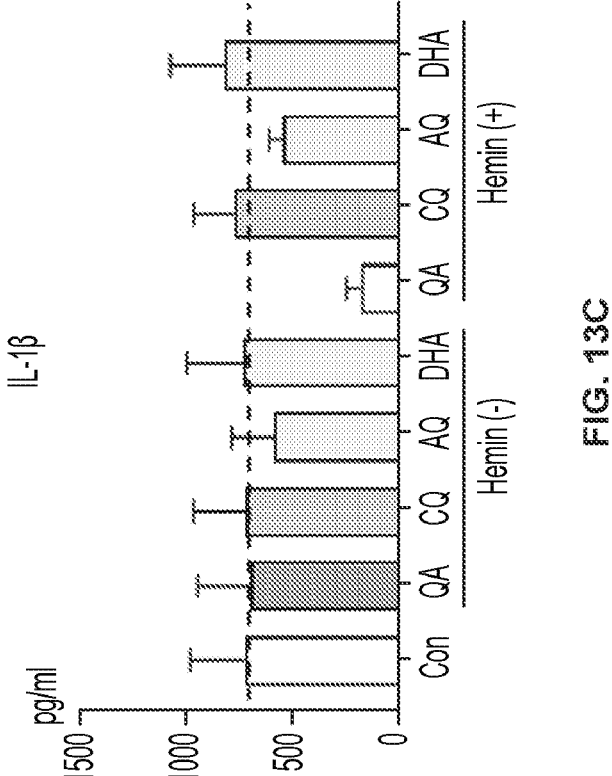
Figure 13D:
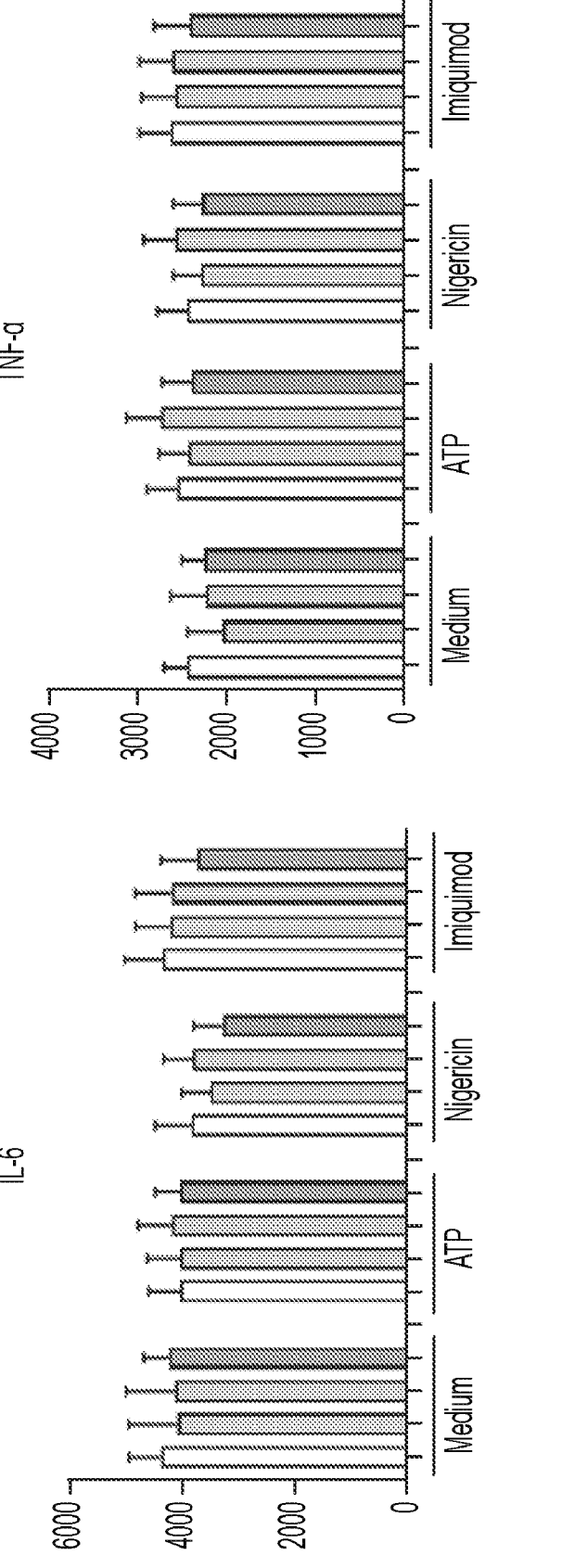
Figure 14:
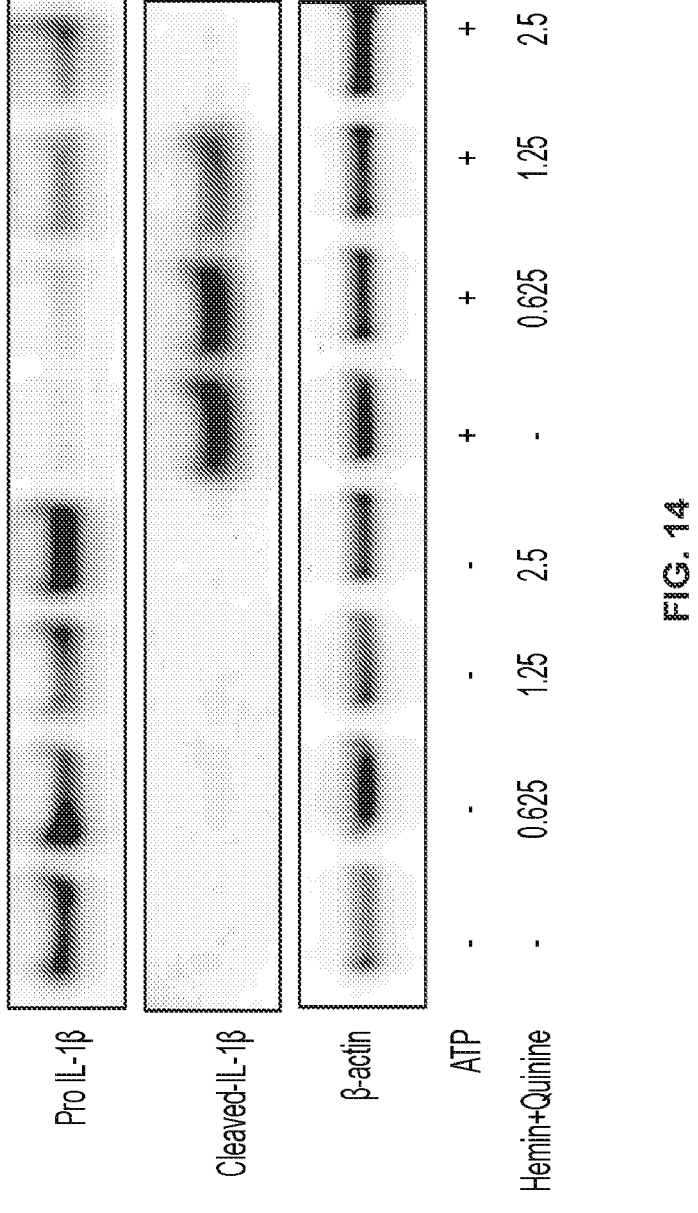
FIG. 14 depicts human monocytes isolated from peripheral blood was cultured with LPS for 3 hours to prime pro-IL-1β production followed by addition of ATP to trigger IL-1β cleavage without or with 2.5 μM hemin plus quinine. After 30 min, cells were harvested and levels of pro-IL-1β and cleaved IL-β analyzed by western blot.

Our findings presented here demonstrate that hemin plus quinine (Q+H), but not hemin alone or quinine alone, inhibits NLRP3 inflammasome pathway in human monocytes activated through multiple NLRP3 agonists including ATP, nigericin, and imiquimod (FIG. 13A). The effect of Q+H was dose-dependent with almost complete inhibition of IL-1$\beta$ production at the highest tested concentration (2.5 $\mu$M) (FIG. 13B). Inhibition of inflammasome by Q+H was specific to the heme binding ability of quinine since other hemin binding small molecules such as chloroquine (CQ), amodiaquine (AQ), and dihydroartemisinic (DHA) (FIG. 13C) had no inhibitory effect on the inflammasome activation pathway. In addition. Q+H did not alter the expression of IL-6 and TNF-$\alpha$ (FIG. 13D), indicating that the effect is specific to the inflammasome activation pathway rather than overall cell activation. Further support for inhibition of inflammasome activation pathway was the demonstration that Q+H prevented cleavage of pro-IL-1$\beta$ into active IL-1$\beta$ as shown by Western blotting (FIG. 14).

Figure 15:
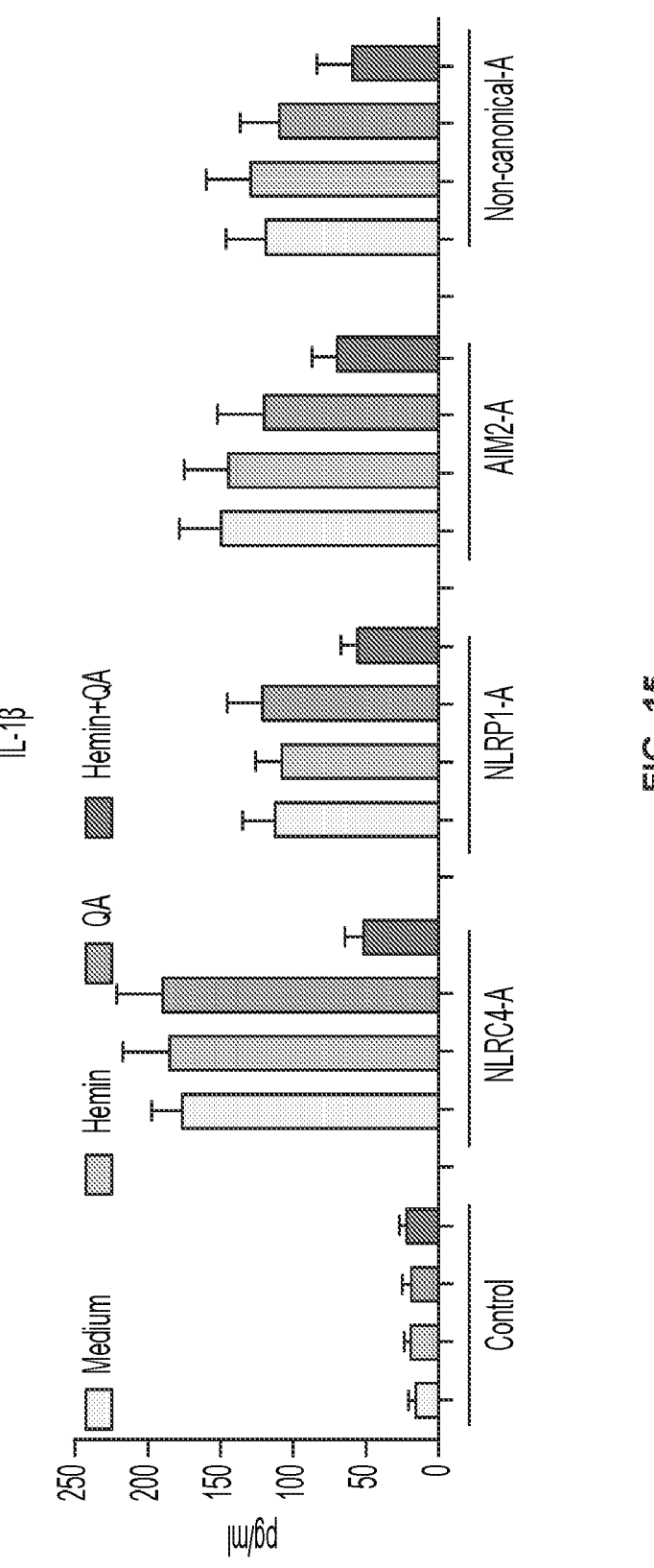
FIG. 15 depicts human monocytes isolated from peripheral blood cultured with LPS for 3 hours to prime pro-IL-1β production followed by addition of NLRC4, NLRP1, AIM2 and non-canonical inflammasome pathway agonists to induce IL-1β secretion together with hemin, quinine or hemin plus quinine. Levels of IL-1β level in the culture medium at 3 hours post addition of agonists are shown.

In addition to NLRP3 inflammasome pathway, Q+H was able to inhibit all inflammasome signaling pathways (FIG. 15).

Figure 16A:
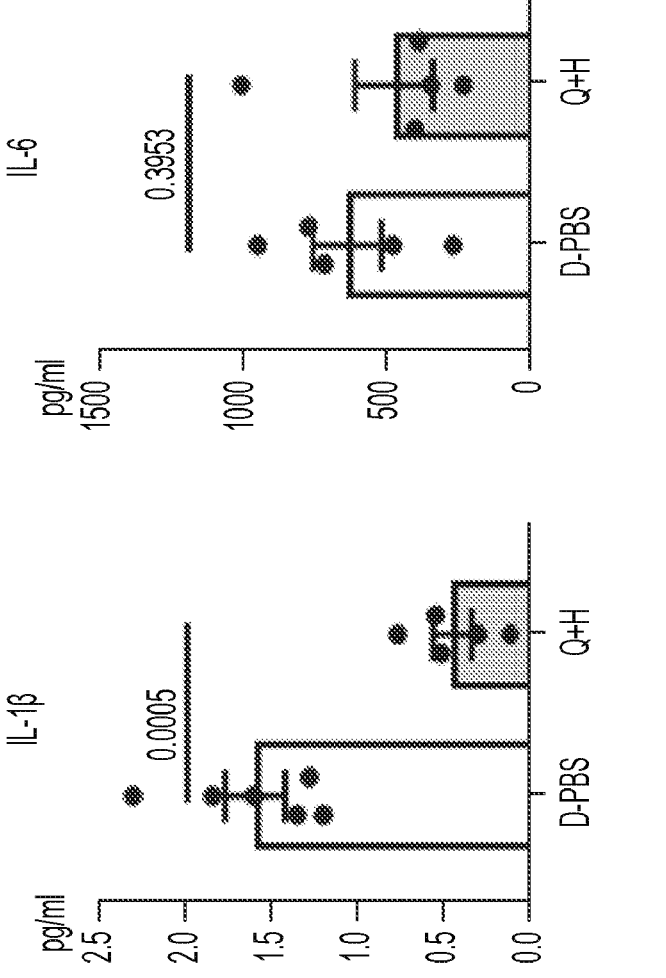
FIG. 16A-B: Mice were I.P. injected with alum (700 μg/mice) along with D-PBS as control or quinine+heme (Q+H) as treatment. Levels of IL-1β, IL-6 (FIG. 16A) as well as numbers of white blood cells, including neutrophil, monocyte T and B cells (FIG. 16B) in the peritoneal cavity at 16 hours post injection are shown.
Figure 16B:
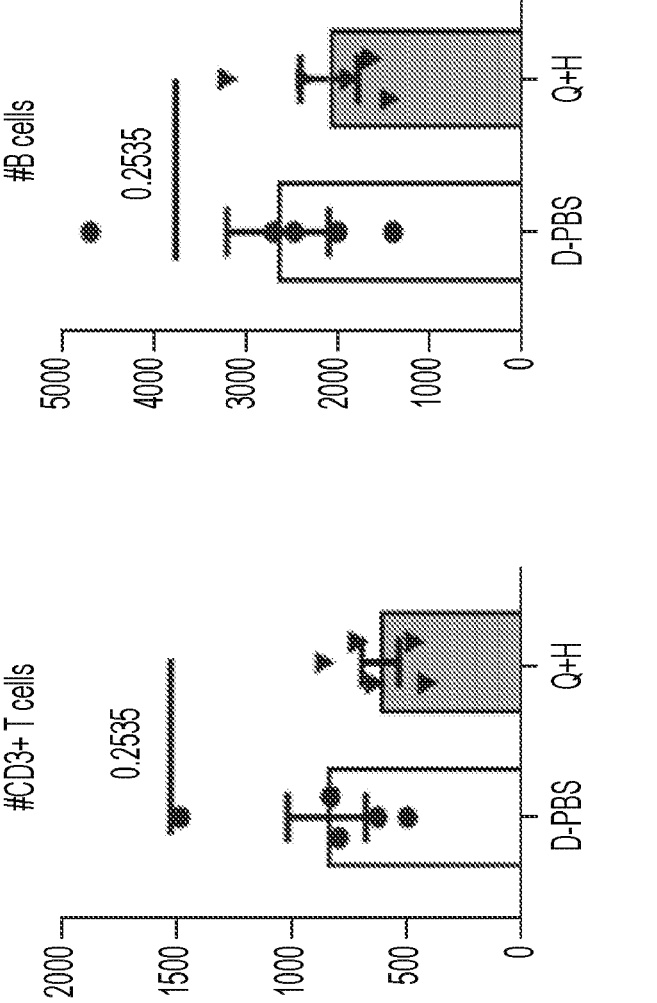

Alum-induced peritonitis is classically used as an inflammasome-dependent inflammation animal model. Alum I.P. injection increases IL-1$\beta$ and other inflammatory cytokine production as well as induces the migration of neutrophils and monocytes into the peritoneum. We found that Q+H inhibited alum-mediated IL-1$\beta$ secretion (FIG. 16A) and inflammatory cell migration in vivo (FIG. 16B).

Figure 17B:
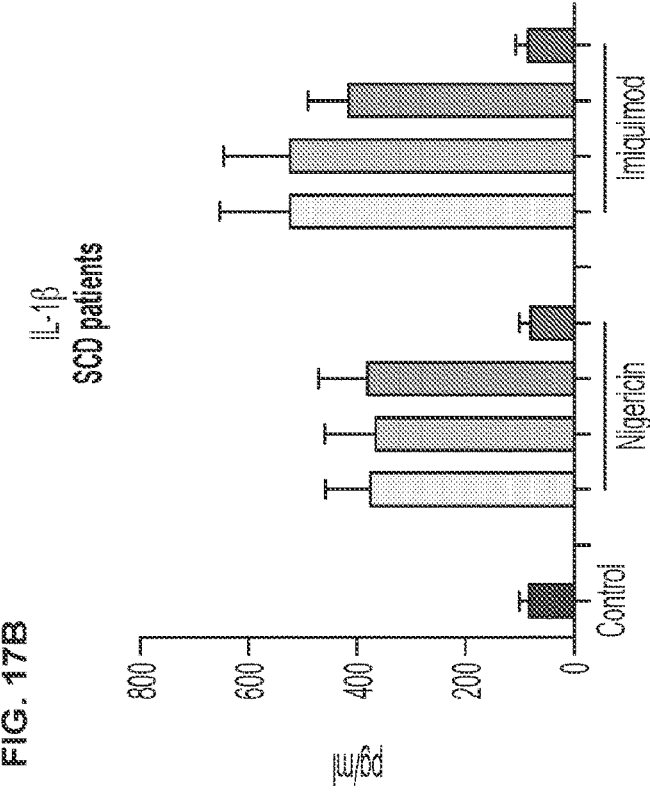
FIG. 17A-B.
Figure 17A:
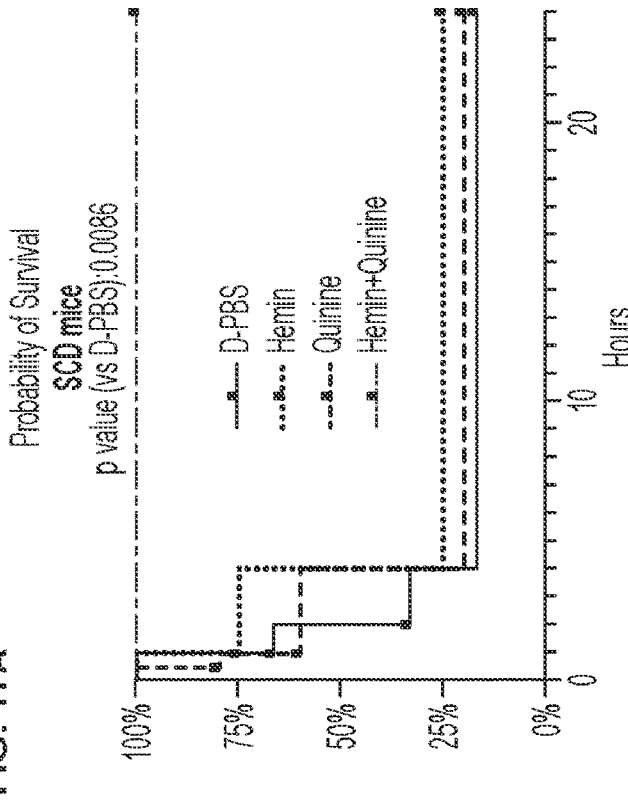

SCD mice are more sensitive to inflammatory stimuli than control mice. 80% of sickle mice (but none of the control mice) died following I.P. injection with alum whereas all survived if they had been treated with Q+H ((40 $\mu$g quinine+80 $\mu$g hemin)/mouse, I.P. injection) (FIG. 17A). Using monocytes from SCD patients, we also found inhibition of inflammasome activation by Q+H (FIG. 17B).

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of treating a vaso-occlusive crisis in a patient having sickle cell disease, comprising administering to a patient in need thereof a therapeutically effective dose of quinine base or quinine salt or a combination of quinine base or quinine salt and hemin.

2. The method of claim 1, wherein the patient exhibits hemolysis.

3. The method of claim 1, wherein the method comprises administration of a therapeutically effective dose of quinine base or quinine salt alone.

4. The method of claim 1, wherein the method comprises administration of a therapeutically effective dose of a combination of quinine base or quinine salt and hemin.

5. The method of claim 1, wherein the combination of quinine base or quinine salt and hemin inhibits inflammasome activation in innate immune cells leading to decreased inflammatory cytokine production.

6. The method of claim 1, wherein the inhibition by quinine base or quinine salt alone occurs in the presence of hemolysis or free heme in the blood.

7. The method of claim 1, wherein the inhibition by quinine base or quinine salt alone does not occur in the absence of hemolysis or free heme in the blood.

8. The method of claim 1, wherein the inhibition by the combination of quinine base or quinine salt and hemin does not depend on the presence of endogenous free heme in the blood.

9. The method of claim 4, wherein the patient exhibits low or no in vivo hemolysis.

10. The method of claim 1, wherein exogenous hemin is not administered.

11. The method of claim 1, wherein the method comprises inhibiting inflammatory cytokines production in the patient.

12. The method of claim 1, wherein the method comprises reducing anemia in the patient.

13. The method of claim 1, wherein the method comprises reducing vascular occlusion in the patient.

14. The method of claim 1, wherein the method comprises reducing tissue damage in injury.

15. A method of treating a vaso-occlusive crisis in a patient having sickle cell disease, comprising administering to a patient in need thereof a therapeutically effective dose of a combination of quinine base or quinine salt and hemin, wherein the combination of quinine base or quinine salt and hemin is in a dose effective in inhibiting NLRP3 inflammasome pathway in a patient.

* * * * *